// United States Patent //

Clemens et al.

(10) Patent No.: US 9,086,371 B2
(45) Date of Patent: Jul. 21, 2015

(54) FLUIDICS DEVICES

(75) Inventors: Charles E Clemens, Encinitas, CA (US); Robert Mucic, Glendale, CA (US); Rudolph A. Montalvo, Woodland Hills, CA (US); Clark Foster, Mission Viejo, CA (US); Gary R. Gust, Huntington Beach, CA (US); Thomas P. Robinson, Encinitas, CA (US); Gary T. Olsen, La Crescenta, CA (US)

(73) Assignee: OSMETECH TECHNOLOGY, INC., Carlsbad, CA (US)

( * ) Notice: Subject to any disclaimer, the term of this patent is extended or adjusted under 35 U.S.C. 154(b) by 0 days.

(21) Appl. No.: 13/551,403

(22) Filed: Jul. 17, 2012

(65) Prior Publication Data

US 2013/0137591 A1    May 30, 2013

Related U.S. Application Data

(60) Continuation of application No. 12/534,681, filed on Aug. 3, 2009, now abandoned, which is a division of application No. 12/032,356, filed on Feb. 15, 2008, now Pat. No. 7,863,035.

(60) Provisional application No. 60/890,180, filed on Feb. 15, 2007, provisional application No. 60/953,197, filed on Jul. 31, 2007.

(51) Int. Cl.
*B01L 3/00*     (2006.01)
*G01N 27/27*   (2006.01)
(Continued)

(52) U.S. Cl.
CPC .......... *G01N 27/27* (2013.01); *B01L 3/502715* (2013.01); *B01L 3/502738* (2013.01); *B01L 3/502707* (2013.01); *B01L 3/502723* (2013.01); *B01L 7/52* (2013.01); *B01L 7/525* (2013.01); *B01L 9/527* (2013.01); *B01L 2200/025* (2013.01); *B01L 2200/027* (2013.01); *B01L 2200/0684* (2013.01); *B01L 2200/10* (2013.01); *B01L 2300/023* (2013.01); *B01L 2300/024* (2013.01); *B01L 2300/0636* (2013.01); *B01L 2300/0645* (2013.01); *B01L 2300/088* (2013.01); *B01L 2300/0816* (2013.01); *B01L 2300/0867* (2013.01); *B01L 2300/0874* (2013.01);
(Continued)

(58) Field of Classification Search
USPC .............. 422/50, 430, 68.1, 81, 82.01–82.04, 422/502–505, 113; 435/4, 6.1–6.19, 7.1, 435/7.72, 7.9–7.95, 287.1–287.3, 287.8, 435/287.9, 288.2–288.5; 436/518, 524, 436/525, 529–532
See application file for complete search history.

(56) References Cited

U.S. PATENT DOCUMENTS 5,620,850 A    4/1997 Bamdad et al.
6,197,515 B1   3/2001 Bamdad et al.
(Continued)

OTHER PUBLICATIONS

Laser et al., "A review of micropumps," *J. Micromech. Microeng.*, 14:R35-R64 (2004).
(Continued)

*Primary Examiner* — Melanie Y Brown
*Assistant Examiner* — Erik B Crawford
(74) *Attorney, Agent, or Firm* — Morgan, Lewis & Bockius LLP; Robin M. Silva

(57) ABSTRACT

The invention relates to fluidics as used in medical and diagnostic equipment and relates further to means for purifying, abstracting, filtering, detecting and/or measuring analytes in liquid samples.

17 Claims, 19 Drawing Sheets

(51) Int. Cl.
*B01L 7/00* (2006.01)
*B01L 9/00* (2006.01)

(52) U.S. Cl.
CPC .... *B01L2300/0887* (2013.01); *B01L 2300/123* (2013.01); *B01L 2300/1827* (2013.01); *B01L 2400/0439* (2013.01); *B01L 2400/0442* (2013.01); *B01L 2400/0478* (2013.01); *B01L 2400/0481* (2013.01); *B01L 2400/0487* (2013.01); *B01L 2400/0605* (2013.01); *B01L 2400/0655* (2013.01)

(56) References Cited

U.S. PATENT DOCUMENTS

| | | | |
|---|---|---|---|
| 6,306,584 | B1 | 10/2001 | Bamdad |
| 6,322,979 | B1 | 11/2001 | Bamdad et al. |
| 6,440,725 | B1 * | 8/2002 | Pourahmadi et al. ...... 435/288.5 |
| 6,472,148 | B1 | 10/2002 | Bamdad et al. |
| 6,494,230 | B2 | 12/2002 | Chow |
| 6,548,895 | B1 | 4/2003 | Benavides et al. |
| 6,755,211 | B1 | 6/2004 | O'Connor et al. |
| 6,809,196 | B2 | 10/2004 | Bamdad et al. |
| 7,223,363 | B2 | 5/2007 | McNeely et al. |
| 2001/0036672 | A1 * | 11/2001 | Anderson et al. ............ 436/180 |
| 2003/0002995 | A1 * | 1/2003 | Urano et al. ................ 417/322 |
| 2004/0156753 | A1 | 8/2004 | Roitman et al. |
| 2004/0189311 | A1 * | 9/2004 | Glezer et al. ................ 324/444 |
| 2005/0118647 | A1 * | 6/2005 | Chung et al. ................ 435/7.1 |
| 2005/0173004 | A1 | 8/2005 | Apostolides |
| 2006/0040276 | A1 | 2/2006 | Bamdad et al. |
| 2006/0090800 | A1 | 5/2006 | Banerjee et al. |
| 2006/0102862 | A1 | 5/2006 | Sobek |
| 2006/0160164 | A1 | 7/2006 | Miller et al. |
| 2006/0165559 | A1 | 7/2006 | Greenstein et al. |
| 2006/0207880 | A1 * | 9/2006 | Joyce et al. ................ 204/451 |
| 2007/0059732 | A1 | 3/2007 | Bamdad et al. |

OTHER PUBLICATIONS

Cooper et al., "Poly(dimethylsiloxane) as a Material for Fabricating Microfluidic Devices," *Accounts of Chemical Research*, 35(7):491-499 (2002).

* cited by examiner

FLUIDICS DEVICES

RELATED APPLICATIONS

This application is a continuation of U.S. patent application Ser. No. 12/534,681, now abandoned, which is a divisional of U.S. patent application Ser. No. 12/032,356, filed Feb. 15, 2008, now U.S. Pat. No. 7,863,035, entitled the same, and claims the benefit of U.S. Provisional Patent Applications Nos. 60/890,180, filed Feb. 15, 2007, and 60/953,197, filed Jul. 31, 2007, entitled the same, au of which are incorporated by reference.

FIELD OF THE INVENTION

The invention relates to fluidics as used in medical and diagnostic equipment and relates further to means for purifying, abstracting, filtering, detecting and/or measuring analytes in liquid samples.

BACKGROUND OF THE INVENTION

The following documents are all incorporated herein by reference in their entireties, although none is admitted to be prior or relevant art. Collectively they reflect that there is a current and long-felt need for, and past failure of success as relates to, adequate microcassette fabrication and microfluidics, not only from a cost and ease of fabrication and reproducibility standpoint, but also from the standpoint that such systems are typically restricted to laminar flow and feature inefficient mixing compounded by gaseous bubble formation that obstructs or restricts flow and diffusion. The present invention, depending on aspect and embodiment, provides useful solutions to one or more of these historic deficiencies.

Woolley et al. (1996) report functional integration of PCR amplification and capillary electrophoresis in a microfabricated DNA analysis device. Anal. Chem., 68:40814086. The chips are generated by photolithography and etching of silicone wafers. The prospects for electrophoretic valving and active microfabricated valves made from polymer diaphragms are also discussed.

Martynova et al. (1997) report fabrication of plastic (poly (methylmethacrylate) (PMMA)) microfluid channels by imprinting methods for use in electrophoretic and chromatographic applications. Anal. Chem., 69:4783-4789. Mechanical pumping is referenced, as are the fabrication techniques of casting, molding, laser ablating and machining plastic. Bubble entrapment is noted as a problem that can be solved by heating.

Roberts et al. (1997) report micro channel construction using UV laser machined polymer substrates (e.g., polystyrene, polycarbonate, cellulose acetate, and poly(ethylene terephthalate) (PET) for the development of microdiagnostic systems. Anal. Chem., 69:2035-2042. The article also discusses laminate sealing. Pump and valving are not addressed.

Burns et al. (1998) report an integrated nanoliter DNA analysis device made of a glass and silicone substrate and containing microfabricated channels, heaters, temperature sensors, and fluorescence detectors. Science, vol. 282, pp. 484-487. The device is made using photolithography and is reportedly capable of measuring, mixing, amplifying and digesting DNA.

Kopp et al. (1998) report continuous-flow PCR on a glass microchip. Science, vol. 280, pp. 1046-1048.

Waters et al. (1998) report a microchip device for cell lysis, multiplex PCR amplification, and electrophoretic sizing and fluorescence-based detection. Anal. Chem., 70:158-162. Microchannels are polymer-etched and 50 um wide by 10.4 um deep. Valving, pumps, and the identity of the polymer substrate are not addressed.

Duffy et al. (1999) report microfabricated centrifugal microfluidic systems having microscopic channels formed in a plastic disk by casting molded PDMS or machining pmethylmethylacrylate. Anal. Chem. 71:4669-4678. The channels are reported to have diameters of 5 um-0.5 mm and depths of 16 um-3 mm.

Anderson, J. et al. (2000) report fabrication of three-dimensional microfluidic systems in PDMS using "membrane sandwiches", in which thin membranes having channel structures molded on each face are fixed under pressure between two thicker, flat slabs. Anal. Chem. 72, pp 3158-3164.

Anderson, R. et al. (2000) report a miniaturized integrated polycarbonate device ("disposable cartridge") the size of a credit card for automated multistep genetic assays. Nucl. Acid. Res., Vol. 28, No. 12, pp. i-vi. The device employs laminate valves made out of a 0.01 mm thick mylar held in place by ultrasonic welding or adhesives. Fluids are moved therethrough using a pneumatic diaphragm valve and vacuum. Porous hydrophobic membranes are reported that allow the passage of gas but not liquids.

Barker et al. (2000) report polystyrene, PDMS, polycarbonate and polyethylene terephthalate glycol (PETG) plastic microfluidic devices having surfaces modified with polyelectrolyte multilayers (PEMs). Anal. Chem. 72: 4899-4903.

Beebe et al. (2000) report a PDMS microfluidics platform that combines liquid-phase photopolymerization cartridges using lithography, channels, pH-actuated hydrogel valving, and sensors. PNAS, vol. 95, no. 25, pp. 13488-13493.

Liu et al. (2000) report chaotic advection passive mixing in a three-dimensional serpentine microchannel having a C-shaped repeating unit. J. Micro-electromech. Sys., Vol. 9 No. 2, pp. 190-197. The device is fabricated in a silicon wafer using a double-sided KOH we-etching. Discussed are active mixing techniques versus passive techniques, the relative sophistication and difficulties presented by the former, and the need for at least one such mechanism when small dimension (tens of micrometers) channels are employed. Also discussed is the fluid dynamics principle of Reynolds numbers, $R_e = Q/A$ (flow rate over cross-sectional area)$\times D_h/v$ (hydraulic diameter of channel over kinetic viscosity of fluid. The repeating C— units emanate away from the inlet and toward a distinct outlet.

Oleschuck et al. (2000) report trapping of bead-based reagents within microfluidic systems and on-chip solid-phase extraction and electrochromatography, coupled with electrofluorescence detection. Anal. Chem., 72:585-590. The system is made of etched glass and features continuous, valveless flow.

Unger et al. (2000) report on monolithic microfabricated valves and pumps for multilayer soft lithography. Science 288; 113-116. Soft lithography is described as an alternative to silicon-based micromachining and uses replica molding of nontraditional elastomeric materials to fabricate stamps and microfluidic channels, with advantages afforded in terms of rapid prototyping, ease of fabrication and biocompatibility. Systems containing on-off valves, switching valves, and pumps made entirely out of elastomer are described. Those systems include microlectromechanical structures ("MEMS") that are either bulk or surface micromachined from silica or other semiconductor-type materials (e.g., polysilicon, metals, silicon nitride, silicon dioxide, etc.), with the latter sequentially applied and patterned in 3D structures, or else replication molding-based by patterned curing of elastomeric material ("soft lithography"). The elastomer used is a two-component addition-cured silicon rubber fused by hermetic sealing and irreversible bonding. Up to seven (7) independent layers are combined into one using this technique. Each of the layers and resulting device is monolithic (i.e., all made from the same material). The valves described are crossed-channel in architecture, 100 um wide by 10 um high, mediated by polymer membrane typically 30 um in thickness, and sealed with a glass bottom layer. The flexibility and durability of the layers permits the repeated opening and closing of valves upon pneumatic actuation without appreciable fatigue. Tubular flow channels are urged as opposed to rectangular or other shapes, and there is also discussion of the problem of electrolytic bubble formation and avoidance thereof. A peristaltic pump consisting of three valves arranged in a single channel is also reported. The figures also show unidirectional flow in which the inlets are remote from the "waste" outlet points.

Xu et al. (2000) report a room-temperature imprinting method for microchannel fabrication in PMMA. Anal. Chem., 72:1930-1933. PDMS film is used to seal the channels, which are imprinted from a micromachined silicone template. Pumping and valving are not per se addressed.

Chabinyc et al. (2001) report an integrated fluorescence detection system in combination with disposable PDMS microfluidic implements. Anal. Chem., 73:44914498.

Gioradano et al. (2001) report use of the polymerase chain reaction (PCR) in polyimide microchips using 1.7 ul volumes and IR-mediated thermocycling. Anal. Biochem., 291:124-132.

Ismagilov et al. (2001) report multi-phase laminar fluid flow and "switching" through a three-dimensional elastomeric microstructure formed by two microfluidic channels, fabricated in layers that contact one another face-to-face (typically at a 90 angle), with the fluid flows in tangential contact. Anal. Chem. 73:4682-4687. There is no discussion of valves or valving per se, pressure is administered by syringe, polydimethylsiloxane (PDMS) membranes of 4-5 mm in dimension are used in construction, and channels of ~25-200 $\mu$m operative height, 100-400 $\mu$m operative width, and 2-4 cm operative length are used. Further, the inlet and outlet ports are remote to another, the adhesion of the individual layers is accomplished by oxidizing the mating surfaces in an air plasma system for approximately 1 minute, and a glass cover slip is also used.

Kamholz and Yager (2001) theoretically analyze molecular diffusion in pressure-driven laminar flow in microfluidic channels. Biophys. J., 80:155-160. The authors conclude there is reduced diffusivity in microfluidic systems, including, e.g., systems employing self-assembling monolayers (SAMS).

Lachner et al. (2001) report the advantages of planar microchip capillary electrophoresis in conjunction with electrochemistry, including miniaturization potential while preserving sensitivity. Electrophoresis 22:2526-2536. Emphasis is on the selective grounding of a detection reservoir relative to a "separation channel" into which sample is first introduced. The system also features sample waste and buffer reservoirs, as well as a high-voltage source to effect separation. By definition, the system depends on electric field establishment for sample migration and there is no circulation or recirculation of liquid sample. These systems feature glass or plastic chips, with the latter fashioned from laser ablation or injection molding techniques, and a variety of electrode surfaces, including carbon, platinum, palladium, copper and gold. Applications discussed include those for separation and detection of catecholes, amino acids, peptides, carbohydrates, nitroaromatics, PCR products, organophosphates and hydrazines. As expected for electrophoretic applications, separation of PCR products is coordinated with restriction enzyme digestion.

Whitesides et al. (2001) review soft lithograpy techniques and the implications for microfabrication and biochip patterning and configuration. Annu. Rev. Biomed., 3:335-73. Soft lithography, as opposed to photolithography, is based on printing and molding using elastomeric stamps with patterns of interest in bas-relief. PDMS is a substrate of choice that is patterned with self-assembling monolayers (SAMs) and microcontact printing (uCP). Membrane-stacking is noted as a method of synthesizing and configuring 3-dimensional microfluidic structures. Pumps (including pneumatic) and soft PDMS membrane flap valving is also briefly noted.

Yuen et al. (2001) report a microchip module of blood sample preparation and nucleic acid amplification reactions. Genome Res., 11:405-412. The module is a computer numerical control-machined Plexiglas microchip. A syringe pump is used in tandem with valving.

Auroux et al. (2002) review micro analysis systems for the period 1997 to 2002. Anal. Chem. 74: 2637-2652.

Beebe et al. (2002) review microfluidics in general and the fabrication of valves, mixers and pumps for the same as of 2002. Annu. Rev. Biomed. Eng. 4:261-86. Micromatching, soft lithography, embossing, in situ construction, injection molding and laser ablation are discussed, as well as the advantages and disadvantages attendant thereto.

Jeon et al. (2002). Report design and fabrication of integrated passive valves and pumps for flexible polymer 3-dimensional microfluidic systems. Biomed Microdevices 4:117-121.

Johnson et al. (2002) report rapid microfluidic mixing in preformed T-microchannel imprinted in a hot-imprinted polycarbonate silicon stamped substrate and modified with a pulsed UV excimer laser to create slanted wells at the junction. Anal. Chem. 74:45-51. PETG "lids" were sealed to the PC by heat-bonding.

Stroock et al. (2002) report chaotic mixers for microchannels. Science 295: 647-651. The difference between laminar and turbulent flow is discussed in terms of efficient mixing, with the former (characteristic of systems having channels of dimension ~100 $\mu$m or less) described as less efficient and characteristic of microfluidic systems in general. Stroock et al.'s solution is to employ textured relief structures deposited by planar lithographic techniques inside PDMS microfluidic channels in order to impart differential resistance across varied topographic surfaces, thereby improving passive mixing in the process.

Klank et al. (2002) report $CO_2$ laser micromachining and back-end processing for rapid production of PMMA-based microfluidic systems. Lab Chip, 2:242-246.

McDonald and Whitesides (2002) report poly(dimethylsiloxane) (PDMS) as a useful material for fabricating microfluidic devices. Accounts of Chemical Res., vol. 35, no. 7, pp. 491499. Silicone adhesive tapes are noted for their ability to reversibly effect water-tight binding between different PDMS components. 3-D "membrane sandwich" fabrication by stacking multiple layers is also discussed, as is the ability to configure the devices with chambers that fit pipette tips.

Pugmire et al. (2002) report surface characterization of laser-ablated polymers used for microfluidics. Anal. Chem., 74:871-878. Electroosmotic flow comparisons are made between PMMA, PETG, PVC and PC after ablation under different gaseous conditions. Pumping and valving are not addressed.

Qi et al. (2002) report high-aspect-ration microstructures (HARMS) in microfluidic devices fabricated from PMMA using hot-embossing with integrated sampling capillary and fiber optics for fluorescence detection. Lab Chip, 2:88-95. Aspect ratio is described as the ratio of feature height to lateral dimension. Pumping and valving are not addressed.

Reyes et al. (2002) briefly review the historical evolution of micro total analysis systems ("uTAS"; synonymous with "lab on a chip") theory and technology, including microfabrication, bonding, surface modification, design, interfaces and connections, microvalves and flow control, and micropumps. Anal. Chem. 74:2623-2636. Construction materials noted include, e.g., PDMS, PMMA, PC, poly(ethyleneterephthalate) (PET), and poly(tetrafluoroethylene) (Teflon®). Valving and pumping are generally discussed on page 2631 et seq. Passive membraneous check valves are noted, as well as flap, lever and duckbill varieties.

Wang, J. (2002) reports on electrochemical detection in microscale analytical systems and how such systems offer possible advantages by way of miniaturization, portability and, more tenuously, disposability. Talanta 56:223-231. Emphasis is again on electrophoretic separations and sample reservoir to waste reservoir directionality and flow, with the reservoirs made of PDMS/glass. Included is discussion of capillary electrophoretic (CE) systems, micromachining and ablation techniques, as well as discussion of different electrode types/compositions and forms of electronic detection, e.g., fixed-potential/current monitoring (amperometric) and voltammetry. Detection of nucleic acids is discussed using intercalating iron-phenanthroline redox markers.

Breadmore et al. (2003) report microchip-based purification of DNA from biological samples. Anal. Chem. 75:1880-1886.

Fiorini et al. (2003) report fabrication of thermoset polyester microfluidic devices and embossing masters using rapid prototyped polydimethylsiloxane (PDMS) molds. Lab Chip, 3:158-163.

Glasgow and Aubry (2003) report enhanced microfluidic mixing using time pulsing. Lab Chip, 3:114-120. Mixing is accomplished by time varying and pulsing fluid flow using, e.g., variable channel dimensions. Bubble entrapment is stated as a problem to be avoided. The substrate used is not identified and there is no discussion of venting or valving.

Jensen et al. (2003) report microstructure fabrication in poly(methyl methylacrylate) (PMMA) with a $CO_2$ laser system, including raster scanning to produce cavities 50 um wide and 200 um deep. Lab Chip, 3:302-307.

Koh et al. (2003) report integrated PCR, valving and electrophoresis in a plastic device for bacterial detection. Anal. Chem. 75:45914598. The device is made from cyclic polyolefin having graphite ink electrodes and photopatterned gel domains that function as passive valves. Detection is optical and accomplished using laser-induced fluorescence of an interchalating dye. Volumes used were 29-84 nL.

Kricka and Wilding (2003) review microchip PCR systems bearing serpentine channels and fabricated from molded PDMS, micromachined polycarbonate or assembled layers of ceramic tape, held together, e.g., by use of adhesives. Anal. Bioanal. Chem. 377:820-825. A host of passivation agents are also discussed that avoid adverse surface interactions, including, e.g., silicon oxide, PDMS, polypropylene, BSA, and polyvinylpyrrolidone.

Landers (2003) reports inter alia on the potential for performing single nucleotide polymorphism (SNP) diagnostics on electrophoretic microchips, preferably using optical detection on capillary based systems. Anal. Chem., 75:2919-2927. See, e.g., pp. 2922.

Liu et al. (2003) report sophisticated microfluidic PCR systems devised of multilayer elastomeric PDMS formed using photolithography and active pumping and valving schemes. Anal. Chem. 75:4718-4723.

Wang et al. (2003) report low-density microarrays assembled in microfluidic chips fabricated from hot-embossed PMMA for the detection of low-abundant DNA mutations. Anal. Chem., 75:1130-1140. Appropriate ligand linking chemistry is also addressed.

Buch et al. (2004) report DNA mutation detection in a modular polycarbonate microfluidic network using temperature gradient gel electrophoresis. Anal. Chem. 76:874-881. One module is embossed with microchannels and the other contains a tapered microheater lithographically patterned along with an array of temperature sensors.

Gustafsson et al. (2004) report integrated peptide sample preparation and MALDI Mass Spectometry on a Microfluidic Compact Disk, in which sample fluid is pushed using centripetal force. Anal. Chem. 76:345-350.

Hashimoto et al. (2004) report rapid PCR in a continuous flow embossed polycarbonate device. Lab Chip, 4:638-645. Microchannel dimensions used were 6 cm (L)×50 um (W)× 150 um (H).

Howell et al. (2004) report on fluid dynamics principles and the design and evaluation of a Dean vortex-based micromixer on a machined PMMA chip. Lab chip, 4:663-669. A double-sided adhesive tape is used to fix the machined chip to a glass slide and bubble avoidance is urged.

Lagally et al. (2004) report an integrated portable genetic analysis microsystem for pathogen/infectious disease detection using PCR, electrophoresis and laser-excited fluorescence detection. Anal. Chem., 76:3162-3170. The system is said to be of etched glass wafer design and contain active solenoid PDMS "membrane valves", with one particular configuration possessing three such valves in series to collectively form a "diaphragm" pump. Sample volumes are 200 nL.

Lai et al. (2004) report a resin-gas injection packaging technique for bonding and surface modification of polymer-based microfluidic platforms such as glass, silicon, polyethylene, polystyrene poly(methyl methacrylate) (PMMA), polyamide, and polycarbonate. Anal. Chem., 76:1175-1183. Also noted are adhesive layer techniques and the problem of bubble accumulation/obstruction and the suggestion to use a vacuum to minimize such.

Laser and Santiago (2004) review micropump structures in J. Micromech. Microeng., 14:R35-R64. The detrimental problem of bubbles in microfluidic systems is noted repeatedly throughout, as is the general dearth of effective pumping systems in microfluidics systems. Despite this, reciprocating pneumatically-driven diaphragm pumps flanked by passive check valves are discussed in the context of multilayer constructions, see, e.g., FIG. 1. and §2.1, although diaphragms made out of soft polymer membranes are said to be a "concern" because of stability. Etching, micromachining and photolithography are also discussed as means of creating device channels and chambers.

Noerholm et al. (2004) report a disposable polycarbonate microfluid chip for online monitoring of microarray hybrizations. Lab Chip, 4:28-37. The chip is 25×76×1.1 mm in dimension and manufactured by micro injection molding. The chip is said to contain an inlet, a 10 ul hybridization chamber, a waster chamber and a vent to allow air to escape when sample is injected. Its utility is demonstrated using hybridization buffer, wash buffers, fluorescence-based detection and a computer controlled syringe pump. The system would appear to be capillary-action mediated, continued flow, non-recirculating and valveless. Use of plastic polymers is said to endow advantages by way of milling, laser ablation, hot embossing and injection molding. The use of adhesive tape in fashioning microstructures is also noted. The problem of bubble development is also noted but the vent used is located remote to the inlet and proximal to a waste chamber.

Schonfeld et al. (2004) report an optimized split-and-recombine (SAR) micro-mixer formed from milled PMMA and featuring active, uniform "chaotic" mixing. Lab Chip, 4:65-69.

Vilkner et al. (2004) review various micro total analysis systems (uTAS), including microfabrication, bonding techniques, microvalves and flow control, and micropumps. Anal. Chem., 76:3373-3386. Their review builds on that of Reyes (2002) and, in addition to discussing PDMS, PMMA, PC, poly(ethyleneterephthalate) (PET), and poly(tetrafluoroethylene) (Teflon®) as construction materials, and general valving, further includes discussion, e.g., of thermoresponsive hydrogel plugs and valving.

Yaralioglu et al. (2004) report ultrasonic mixing in PDMS microfluidic channels using integrated piezoelectric transducers. Anal. Chem., 76:3694-3698.

Fiorini and Chiu (2005) review disposable microfluidic device fabrication, function and application. BioTechniques vol. 38, no. 3, pp. 429-446. Methods of fabrication include replica and injection molding, embossing, and laser ablation. Fluid pumping and valving is also described, as is mixing and analyte separation and detection. Deformable membrane pressure pumps and valves are particularly discussed at pp. 434-5, as is the concept of pulsatile flow. Strategies for mixing include use of 3-dimensional serpentine channels. P. 435. Multilayer fabrication with plastics is also mentioned, as are electrochemical detection schemes and advantages attendant thereto, and nucleic acids as detectable analyte. pp. 438-9.

Howell et al. (2005) report a microfluidic mixer with grooves placed on the top and bottom of milled PMDA channels. Lab Chip, 5:524-530.

Klapperich et al. (2005) report hot-embossed fabrication of a cyclic polyolefin microfluidic device for on-chip isolation of nucleic acids onto silicon particles embedded in the device, followed by elution. Proc. ICMM2005, $3^{rd}$ Int. Conf. on Microchannels and Minichannels. Toronto, CANADA.

Lee et al. (2005) report development of a passive 3-dimensional PDMS micromixer based on repeated fluid twisting and flattening of the channels, and its application to DNA purification. Anal. Bioanal. Chem., 383:776-782. Multi-layer stacking and multi-step photolithography are noted as device fabrication techniques. The system has discreet inlets and outlets that are remote relative to one another.

Roper et al. (2005) report advances in polymerase chain reaction (PCR) methodology on polycyclic olefin microfluidic chips using hydraulic valves and pneumatic pumps. Anal. Chem., 77:3887-3894. Reported reaction volumes are approximately 30 nl.

Skelley et al. (2005) report development and evaluation of a sophisticated capillary electrophoresis microdevice made of glass wafers and PDMS membranes for amino acid biomarker detection and analysis use on Mars. PNAS, vol. 102, no. 4, pp. 1041-1046. The device is vacuum driven and said to possess 34 individual membrane valves and 8 pumps. The wafers are 10 cm in diameter with 20 um deep×70 um wide× 21.4 cm long channels.

Wang et al. (2005) report label-free detection of small-molecule-protein interactions using nanowire nanosensors (silicone; SiNW) and field effect transistors (FETs) on a surface plasma resonance (SPR)-like chip. PNAS, vol. 102, no. 9, pp. 3208-3212.

Whitesides et al. (2005) report a technique for storing and delivering a sequence of reagents to a microfluidic device. Abstract, Anal. Chem., 77(1):64-71. The technique makes use of cartridges of tubing filled by sequentially injecting plugs of reagents separated by air spacers.

Liu et al. (2006) report integrated microfluidic biochips for DNA microarray analysis by fluorescence imaging that contain electromechanical pumps, low-cost check valves, fluid channels and reagent storage containers. Expert Rev. Mol. Diagn., 6(2):253-261 (Abstract).

Soper et al. (2006) forecast point-of-care (POC) biosensor systems for cancer diagnostics/prognostics. Biosensors and Bioelectronics, 21:1932-1942. The article only generally speaks to the future of the field and the need for mass-production, low cost fabrication and specialized valving and pumping systems. Techniques contemplated for construction of such devices include injection molding, nanoprint lithography and hot-embossing.

U.S. Pat. Nos. 7,101,509 and 6,368,871 assigned to Cepheid share a common specification and collectively report and claim temperature controlled devices and methods for the manipulation of materials in a fluid sample using a plurality of microstructures bearing insulator films (selected from silicon dioxide, silicon carbide, silicon nitride, and electrically insulating polymers). The devices employ integrated loading chambers, reaction vessels, and aspirators in connection with the insulator-film bearing structures. Application of a voltage to the structures induces the desired electrophoretic separation and attraction, followed by washing and elution steps. U.S. Pat. Nos. 6,893,879, 6,664,104 and 6,403,037 assigned to Cepheid report and claim similar analyte flow, capture and elution techniques and devices.

U.S. Pat. No. 6,818,185 reports and claims a cartridge for conducting a chemical reaction that consists of a body having at least first and second channels formed therein, a reaction vessel extending from the body, a reaction chamber, an inlet port connected to the reaction chamber via an inlet channel, and an outlet port connected to the reaction chamber via an outlet channel. The inlet port of the vessel is connected to the first channel in the body, and the outlet port of the vessel is connected to the second channel in the body. The walls of the reaction chamber contain polymeric films, and vents for exhausting gas from the second channel are also described. The system also employs differential pressure sources for forcing sample through the system, which can further include thermal surfaces, heating elements, mixing and lysing chambers, and optically transmissive walls.

U.S. Pat. No. 6,374,684 reports a fluid control and processing system having a plurality of chambers and a valve body that includes a fluid sample processing region coupled with a fluid displacement region, the fluid displacement region depressurizable to draw fluid into the fluid displacement region and pressurizable to expel fluid from the fluid displacement region.

U.S. Pat. Nos. 6,830,936, 6,197,595, 6,043,080, 5,922,591, and 5,856,174, each entitled "Integrated nucleic acid diagnostic device" and assigned to Affymetrix, describe and/or claim diaphragm or controllable valve actuated miniature fluid flow systems for measuring and processing fluid samples. The systems described make use of a plurality of different chambers and channels, as well as inlet and vent ports. U.S. Pat. Nos. 6,733,977 and 6,168,948 are similar to these in content.

U.S. Pat. No. 7,223,363 (entitled "Method and System for Microfluidic Interfacing to Arrays") and U.S. Pat. No. 7,235,400 (entitled "Laminated Microarray Interface Device"), each assigned to BioMicro Systems Inc., report pump-driven multi-laminate microfluidics systems having a gasket that defines the walls of a reaction chamber (e.g., serpentine), integrated passive valving, diaphragm and multiple bladder use to promote mixing, the possibility for sample (re)circulation and bubble elimination using an external pumping scheme, the relative positioning of multiple such devices such that there is a pitch of 9 mm between devices for ease of loading by a multipipetteman, and the merit of using construction materials that permit visualization/optical assessment of the system.

U.S. Pat. No. 5,063,081 ("Method of manufacturing a plurality of uniform microfabricated sensing devices having an immobilized ligand receptor"), U.S. Pat. No. 5,096,669 ("Disposable sensing device for real time fluid analysis") and U.S. Pat. No. 5,124,661 ("Reusable test unit for simulating electrochemical sensor signals for quality assurance of portable blood analyzer instruments") to I-STAT Corporation discuss inter alia use of a disposable cartridge system that makes use of an internal bladder to manipulate liquid sample.

Micronics, Inc. also holds numerous patents in the field of microfluidics including, e.g., U.S. Pat. No. 7,223,371 ("Microfluidic channel network device"), 6,743,399 ("Pumpless microfluidics"), 6,742,661 ("Well-plate microfluidics"), 6,581,899 ("Valve for use in microfluidic structures"), 6,557,427 ("Capillaries for fluid movement within microfluidic channels") and 6,488,896 ("Microfluidic analysis cartridge").

Numerous patents and papers published by Paul Yager are also germane to the topic of microfluidics and include, e.g., U.S. Pat. Nos. 5,716,852 and 5,972,710 ("Microfabricated diffusion-based chemical sensor"), 6,007,775 ("Multiple analyte diffusion-based chemical sensor"), 6,039,897 ("Multiple patterned structures on a single substrate fabricated by elastomeric micro-molding techniques"), 6,110,354 and 6,790,341 ("Microband electrode arrays"), 6,159,739 ("Device and method for 3-dimensional alignment of particles in microfabricated flow channels"), 6,454,945 ("Microfabricated devices and methods"), Sensors in Biomaterials Science: An Introductory Text, Ratner, B. D. and Hoffman, A. S., Eds. Academic Press, Inc., Orlando, (1996), Low Reynolds number micro-fluidic devices, Proceedings Hilton Head MEMS conference, Solid-State Sensor and Actuator Workshop, 105-108, (1996), Biotechnology at low Reynolds numbers, Biophysical Journal. 71 (6), 3430-3441, (1996), Integration of microelectrodes with etched microchannels for in-stream electrochemical analysis, Micro Total Analysis Systems, 105-108 (1998), Design of microfluidic sample pre-conditioning systems for detection of biological agents in environmental samples, SPIE Proceedings, 3515, 252-259 (1998), Whole blood diagnostics in standard gravity and microgravity by use of microfluidic structures (T-sensors), Mikrochimica Acta, 131, 75-83 (1999), A novel microfluidic mixer based on successive lamination, Micro Total Analysis Systems, Mesa Monographs, 495-498 (2003), On the importance of quality control in microfluidic device manufacturing, Micro Total Analysis Systems, Mesa Monographs, 1069-1072 (2003), Lab-on-a-chip and fluorescence sensing on the microscale, Fluorescence Sensors and Biosensors, R. B. Thompson, ed., ISBN 0-8247-2737-1, CRC Press, Boca Raton, Fla., c.400 pp (2005), Rapid, parallel-throughput, multiple analyte immunoassays with on-board controls on an inexpensive, disposable microfluidic device, Micro Total Analysis Systems, Vol. 2, Transducer Research Foundation, Pubs., 1000-1002 (2005), Recirculating flow accelerates DNA microarray hybridization in a microfluidic device, Lab on a Chip, in press.

Microfluidic systems and function is also addressed in patents and publications by Stanford's Stephen Quake, including U.S. Pat. No. 7,232,109 ("Electrostatic valves for microfluidic devices"), 7,216,671, 7,169,314, 7,144,616, 7,040,338, 6,929,030, 6,899,137, and 6,408,878 ("Microfabricated elastomeric valve and pump systems"), 7,143,785 ("Microfluidic large scale integration"), 6,960,437 ("Nucleic acid Microfabricated elastomeric valve and pump systems, 6,793,753 ("Method of making a microfabricated elastomeric valve"), 6,767,706 ("Integrated active flux microfluidic devices and methods"), and "A nanoliter-scale nucleic acid processor with parallel architecture," Nat. Biotechnol, 22:4: 435-9 (2004), "Solving the "world-to-chip" interface problem with a microfluidic matrix." Anal. Chem., 75:18:4718-23 (2003), "Microfluidics in structural biology: smaller, faster em leader better." Curr. Opin. Struct. Biol. 13:5:538-44 (2003), "Integrated nanoliter systems," Nat. Biotechnol., 21:10:1179-83 (2003), "Microfabricated fountain pens for high-density DNA arrays," Genome Res., 13:10:2348-52 (2003), "Microfluidic memory and control devices," Science, 300:5621:955-8 (2003), "Microfluidic large-scale integration," Science, 298:5593:580-4 (2002), "A nanoliter rotary device for polymerase chain reaction," Electrophoresis, 23:10:1531-6 (2002), "Dynamic pattern formation in a vesicle-generating microfluidic device." Phys. Rev. Lett. 86:18:4163-6 (2001), "Monolithic microfabricated valves and pumps by multilayer soft lithography." Science, 288: 5463:113-6 (2000); "From micro- to nanofabrication with soft materials," Science, 290:5496:1536-40 (2000), and "A microfabricated device for sizing and sorting DNA molecules." Proc. Natl. Acad. Sci. USA 96:1:11-3 (1999).

In addition to the foregoing work of others, commonly-owned U.S. Pat. Nos. 7,172,897, 6,960,467, 6,875,619, 6,833,267, 6,761,816, 6,642,046, 6,592,696, 6,572,830, 6,544,734, 6,432,723, and 6,361,958 also speak to microfluidics and microfluidics operations, including integration of individual electronic components and positionment into detection devices, including electrochemical detection devices.

As will be become apparent, the configuration and function of the above third party devices is different from aspects and embodiments of the inventions described herein in one or more of construction, valving, mixing, diaphragm positionment and function, bubble elimination, pump interfacing and recirculation design. These differences give rise to real advantages and prospects for the inventions described herein.

BRIEF SUMMARY OF THE INVENTION

Accordingly, in one aspect the invention provides fluidics devices comprising at least one membranous diaphragm having a first and second side. The first side is for coupling to a pump, and the second side is for fluidic coupling to a flow channel (which can include a detection chamber as a flow channel) and a plurality of check valves. The check valves each comprise a sealing surface comprising a valve seat that allows for regulated flow of fluid through the flow channel and a flexible sealing structure for contacting the valve seat and occluding fluid flow therethrough when in a first position, and for promoting fluid flow therethrough when in a second position. Generally, in this aspect, the diaphragm and the flexible sealing structure are integral to one or more layers of a multilayer assembly (e.g. a multilaminate structure). The plurality of check valves alternate opening and closing in coordinated reciprocal fashion according to alternating positive and negative forces exerted on the diaphragm. In an additional aspect, the device comprises a body comprising a channel (which can be the detection chamber) within for transporting a fluid sample, the channel comprising a situs where an operation is performed on one or more components in the fluid sample. The body also comprises an inlet port for receiving the fluid sample, the inlet port in fluid communication with the channel and also in communication with an enclosed gaseous environment. The inlet port can be configured to receive the fluid sample from a pipette tip, including micropipette tips. The body also comprises an outlet port in fluid communication with the inlet port such that upon operation of the device the fluid sample is recirculated through the channel to release gaseous bubbles into the enclosed gaseous environment while simultaneously allowing for facilitated diffusion and performance of the operation on the one or more components in said fluid sample.

In a further aspect, the fluidics devices process no more than about 1.5 mL of fluid at a time, with some aspects processing no more than about 150 ul of fluid at a time. In some aspects, the sample capacity of the device is from about 50 ul to about 200 ul. The channels can comprise a cross-sectional dimension comprising a greater width than height. In some aspects, the channels have a cross-sectional dimension ranging from about 0.030" to about 0.060" in width and from about 0.006" to about 0.014" in height.

In an additional aspect, the fluidics devices are made at least in part from the stacking of multiple individual polymeric laminate sheets, optionally held together by pressure sensitive adhesive sheets. In some aspects, the devices are constructed from alternating laminate and adhesive layers having individual thicknesses in the range of from about 0.0005" to about 0.030". In some aspects, the individual laminate layers are thicker than the individual adhesive layers. In some aspects, the individual laminate layers are from about 0.0005" to about 0.010" thick and said individual adhesive layers are from about 0.001" to about 0.003" thick.

In a further aspect, one or more of the channels of the fluidics devices are formed by grooves, cuts or recesses in one or more of these individual plastic laminate sheets, which can be produced by a die-stamp, laser, chemical etching, or molding.

In an additional aspect, the channels that serve as detection chambers further comprise at least one working electrode in the flow channel, optionally comprising capture binding ligands and SAMs, and thus is optionally a diagnostics device. Thus, aspects of the invention provide for immobilized biological binding partners in the flow/detection channel. These biological binding partners can be immobilized using a self assembling monolayer that is affixed to a surface, optionally an electrode. The biological binding partners can be polynucleotides or proteins (including peptides and antibodies).

In a further aspect, the fluidics devices of the invention further optionally comprise one or more auxiliary electrodes and/or connectors for interface with a detection device. In some aspects, the connectors are configured in a two-dimensional grid of contact points. In some aspects, the connectors may be ZIF connectors and/or side or edge connectors. The fluidics devices can also optional comprise an EEPROM, and/or an internal unused space designed for integration of one or more future functionalities.

In an additional aspect, the fluidics devices of the invention can comprise a transparent or translucent plastic (e.g. an optical window) that permits visualization of circulation and recirculation of the fluid sample within.

In a further aspect, the fluidics devices can comprise one or more valves in fluid communication with the channel for regulating the flow of the fluid sample therethrough. The valves can be check valves, passive valve and bridge valves. In some aspects, or more of the valve seats protrude from a planar structure to promote sealing upon engagement with a corresponding sealing structure. The magnitude of the protuberances relative to the base surface is independently selected from about 0.001" to about 0.005". Optionally, one of more of the valve seats are part of a hollow boss having a plurality of ports adjacent and fluidly coupled to one another in a nonlinear configuration, optionally a "u-structure", and routing fluid from one fluidics plane in the device to one or more other fluidics planes in the device.

In an additional aspect, the fluidics devices can further comprise a means for pumping (e.g. a pump) the fluid sample through the channel. Thus, the devices can comprise a plurality of bridge or check valves actuated by a pneumatic, electromagnetic, or hydraulic pump and a diaphragm. The pneumatic pump can be electrically driven.

In an additional aspect, the devices can further comprise caps for sealing the device following the addition of a sample, and optionally a filter, adsorbent and/or absorbent for reducing or eliminating solutes or analytes in the fluid sample.

In a further aspect, the fluidics devices of the invention further comprise a detector that detects binding events between binding partners and complementary binding partners in a fluid sample, which can be a colorimetric detector or an electronic detector that detects electronic properties of the binding events. In some cases, electrochemiluminescent detection is not preferred. In some cases, fluorescent detection is not preferred.

In an additional aspect, the fluidics devices of the invention are micofluidics devices, filtration devices, or purification or abstraction devices.

In some aspects, particularly when bubble removal is desired, the fluidics devices receives the fluid sample through the inlet port in an upright position of from 15°-90° relative to horizontal and processes the fluid sample in a 15°-90° position relative to horizontal, and wherein the receiving upright position and the processing upright position are not necessarily the same.

In a further aspect, the invention provides racks for carrying a plurality of fluidics devices of the invention, wherein the rack is designed to position said devices relative to one another having a pitch of about 9 mm between successive sample reservoirs of said devices.

In an additional aspect, the invention provides devices that are diaphragm-mediated two-stroke circulation and recirculation devices mediated by passive valving.

In a further aspect, the invention provides diagnostic kits comprising the devices of the invention, and optionally reagents.

In an additional aspect, the invention provides methods of determining the presence, absence and/or amount of analyte in a sample, or analyte binding. The methods comprise providing a fluidics device as outlined herein, adding a sample (usually liquid) suspected of containing one or more of the analytes, circulating and recirculating the sample across the array; and detecting binding of the analytes to the ligands.

DETAILED DESCRIPTION OF THE INVENTION

Figure 1A:
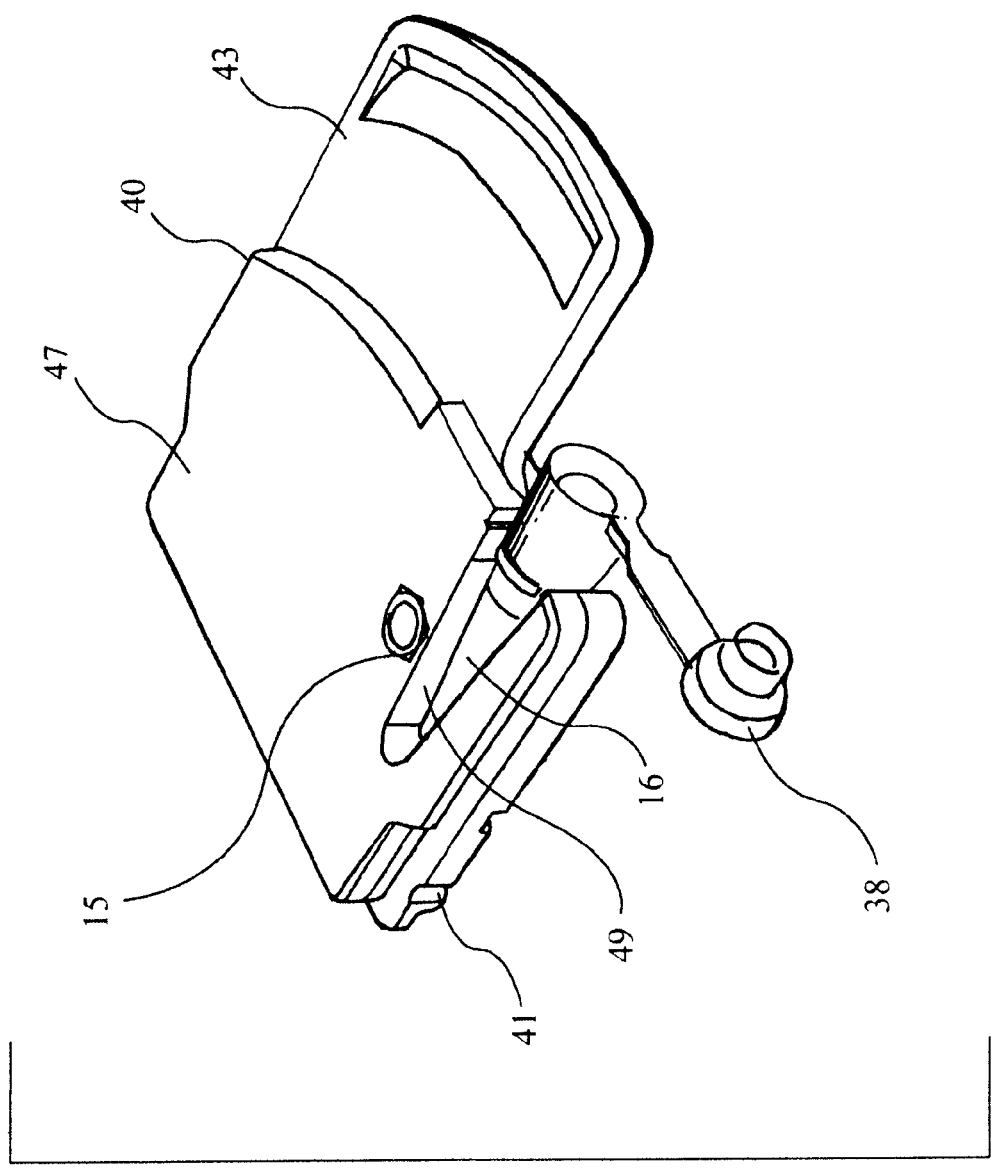
FIG. 1A is a perspective view of a fully assembled fluidics device (cartridge) according to one embodiment of the invention, showing integral handle and cover, integral fill reservoir, pump interface, and cap. Also shown is one of two detents to help align cartridge upon insertion into a cartridge module and provide tactile/audible feedback.

Ease of use and cost considerations are driving systems into a paradigm where inexpensive, disposable consumables are used together with capital equipment. This is especially true in analytic and diagnostic applications where concern over possible contamination of one sample with another leads consumers to prefer single-use devices where feasible. While the inventions discussed here apply more generally to any system configuration and to applications beyond diagnostics, this description will focus on the use of a disposable device—a cartridge—that manipulates sample-specific reagents in concert with separate, reused instrumentation for diagnostic purposes.

Accordingly, in one embodiment the present invention is directed to a fluidics device designed to analyze a plurality of target analytes. In one embodiment the fluidics device of the present invention includes a membranous diaphragm, one side of which, in one embodiment, is coupled to a pump. The second side is coupled to a flow channel, and a plurality of check valves for fluidic coupling. The valves include a sealing surface that include a valve seat allowing for regulated flow of fluid through the flow channel, and a flexible sealing structure for contacting the valve seat and occluding fluid flow through the sealing structure when in a first position and for promoting fluid flow through the seal when in a second position. In one embodiment the diaphragm and flexible sealing structure are integral to one or more layers of a multilayer assembly. The plurality of check valves alternate opening an closing in coordinated reciprocal fashion according to alternating positive and negative forces exerted ion the diaphragm.

In another embodiment the fluidics device includes a body. The body includes a channel within it for transporting a fluid sample. The channel includes a situs where an operation is performed on one or more components in the fluid sample. In addition the body includes an inlet port for receiving the fluid sample. The inlet port is in fluid communication with the channel and also in communication with an enclosed gaseous environment. The body also includes an outlet port in fluid communication with the inlet port such that upon operation of the device the fluid sample is recirculated through the channel to release gaseous bubbles into the enclosed gaseous environment while simultaneously allowing for facilitated diffusion and performance of the operation on the one or more components in the fluid sample.

Thus, the present disclosure provides compositions and methods for detecting the presence or absence of target analytes in samples. As will be appreciated by those in the art, the sample solution may comprise any number of things, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); biological warfare agent samples; research samples (i.e. in the case of nucleic acids, the sample may be the products of an amplification reaction, including both target and signal amplification as is generally described in PCT/US99/01705, such as PCR amplification reaction); purified samples, such as purified genomic DNA, RNA, proteins, etc.; raw samples (bacteria, virus, genomic DNA, etc.); as will be appreciated by those in the art, virtually any experimental manipulation may have been done on the sample.

The methods are directed to the detection of target analytes. By "target analyte" or "analyte" or grammatical equivalents herein is meant any molecule or compound to be detected and that can bind to a binding species, defined below. Suitable analytes include, but are not limited to, small chemical molecules such as environmental or clinical chemical or pollutant or biomolecule, including, but not limited to, pesticides, insecticides, toxins, therapeutic and abused drugs, hormones, antibiotics, antibodies, organic materials, etc. Suitable biomolecules include, but are not limited to, proteins (including enzymes, immunoglobulins and glycoproteins), nucleic acids, lipids, lectins, carbohydrates, hormones, whole cells (including procaryotic (such as pathogenic bacteria) and eucaryotic cells, including mammalian tumor cells), viruses, spores, etc. Particularly preferred analytes are proteins including enzymes; drugs, cells; antibodies; antigens; cellular membrane antigens and receptors (neural, hormonal, nutrient, and cell surface receptors) or their ligands.

In one embodiment, the target analyte is a protein. As will be appreciated by those in the art, there are a large number of possible proteinaceous target analytes that may be detected using the present invention. By "proteins" or grammatical equivalents herein is meant proteins, oligopeptides and peptides, derivatives and analogs, including proteins containing non-naturally occurring amino acids and amino acid analogs, and peptidomimetic structures. The side chains may be in either the (R) or the (S) configuration. In one embodiment, the amino acids are in the (S) or L-configuration. As discussed below, when the protein is used as a binding ligand, it may be desirable to utilize protein analogs to retard degradation by sample contaminants. Suitable protein target analytes include, but are not limited to, (1) immunoglobulins, particularly IgEs, IgGs and IgMs, and particularly therapeutically or diagnostically relevant antibodies, including but not limited to, for example, antibodies to human albumin, apolipoproteins (including apolipoprotein E), human chorionic gonadotropin, cortisol, a-fetoprotein, thyroxin, thyroid stimulating hormone (TSH), antithrombin, antibodies to pharmaceuticals (including antieptileptic drugs (phenyloin, primidone, carbariezepin, ethosuximide, valproic acid, and phenobarbitol), cardioactive drugs (digoxin, lidocaine, procainamide, and disopyramide), bronchodilators (theophylline), antibiotics (chloramphenicol, sulfonamides), antidepressants, immunosuppresants, abused drugs (amphetamine, methamphetamine, cannabinoids, cocaine and opiates) and antibodies to any number of viruses or bacteria outlined below.

As will be appreciated by those in the art, a large number of analytes may be detected using the present methods; basically, any target analyte for which a binding ligand, described below, may be made may be detected using the methods of the invention.

In one embodiment, the target analytes are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with bicyclic structures including locked nucleic acids, Koshkin et al., J. Am. Chem. Soc. 120:13252-3 (1998); positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 69-176). Several nucleic acid analogs are described in Rawls, C & E News Jun. 2, 1997 page 35. All of these references are hereby expressly incorporated by reference. These modifications of the ribose-phosphate backbone may be done to facilitate the addition of ETMs, or to increase the stability and half-life of such molecules in physiological environments.

As will be appreciated by those in the art, all of these nucleic acid analogs may find use in the present invention. In addition, mixtures of naturally occurring nucleic acids and analogs can be made; for example, at the site of conductive oligomer or ETM attachment, an analog structure may be used. Alternatively, mixtures of different nucleic acid analogs, and mixtures of naturally occurring, nucleic acids and analogs may be made.

The nucleic acids may be single stranded or double stranded, as specified, or contain portions, of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. One embodiment utilizes isocytosine and isoguanine in nucleic acids designed to be complementary to other probes, rather than target sequences, as this reduces non-specific hybridization, as is generally described in U.S. Pat. No. 5,681,702. As used herein, the term "nucleoside" includes nucleotides as well as nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

Thus, in one embodiment, the target analyte is a target sequence. The term "target sequence" or "target nucleic acid" or grammatical equivalents herein means a nucleic acid sequence on a single strand of nucleic acid. The target sequence may be a portion of a gene, a regulatory sequence, genomic DNA, cDNA, RNA including mRNA and rRNA, or others. As is outlined herein, the target sequence may be a target sequence from a sample, or a secondary target such as a product of an amplification reaction, etc. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. As is outlined more fully below, probes are made to hybridize to target sequences to determine the presence or absence of the target sequence in a sample. Generally speaking, this term will be understood by those skilled in the art. The target sequence may also be comprised of different target domains; for example, a first target domain of the sample target sequence may hybridize to a capture probe or a portion of capture extender probe, a second target domain may hybridize to a portion of an amplifier probe, a label probe, or a different capture or capture extender probe, etc. The target domains may be adjacent or separated as indicated. Unless specified, the terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain.

Suitable target analytes include biomolecules associated with: (1) viruses, including but not limited to, orthomyxoviruses, (e.g. influenza virus), paramyxoviruses (e.g respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicella-zoster virus, cytomegalovirus, Epstein-Barr virus), rotaviruses, Norwalk viruses, hantavirus, arenavirus, rhabdovirus (e.g. rabies virus), retroviruses (including HIV, HTLV-1 and -11), papovaviruses (e.g. papillomavirus), polyomaviruses, and picornaviruses, and the like; and (2) bacteria, including but not limited to, a wide variety of pathogenic and non-pathogenic prokaryotes of interest including *Bacillus; Vibrio*, e.g. *V. cholerae; Escherichia*, e.g. Enterotoxigenic *E. coli, Shigella*, e.g. *S. dysenteriae; Salmonella*, e.g. *S. typhi; Mycobacterium* e.g. *M. tuberculosis, M. leprae; Clostridium*, e.g. *C. botuliniin, C. tetani, C. difficile, C. perfringens; Cornyebacterium*, e.g. *C. diphtheriae; Streptococcus, S. pyogenes, S. pneumoniae; Staphylococcus*, e.g. *S. aureus; Haemophilus*, e.g. *H. influenzae; Neisseria*, e.g. *N. meningitidis, N. gonorrhoeae; Yersinia*, e.g. *G. lamblia Y. pestis, Pseudomonas*, e.g. *P. aeruginosa, P. putida; Chlamydia*, e.g. *C. trachonmatis; Bordetella*, e.g. *B. pertussis; Treponema*, e.g. *T. palladium*; and the like.

Other suitable target analytes include, but are not limited to, (1) enzymes (and other proteins), including but not limited to, enzymes used as indicators of or treatment for heart disease, including creatine kinase, lactate dehydrogenase, aspartate amino transferase, troponin T, myoglobin, fibrinogen, cholesterol, triglycerides, thrombin, tissue plasminogen activator (tPA); pancreatic disease indicators including amylase, lipase, chymotrypsin and trypsin; liver function enzymes and proteins including cholinesterase, bilirubin, and alkaline phosphotase; aldolase, prostatic acid phosphatase, terminal deoxynucleotidyl transferase, and bacterial and viral enzymes such as HIV protease; (2) hormones and cytokines (many of which serve as ligands for cellular receptors) such as erythropoietin (EPO), thrombopoietin (TPO), the interleukins (including IL-1 through IL-17), insulin, insulin-like growth factors (including IGF-1 and -2), epidermal growth factor (EGF), transforming growth factors (including TGF-n and TGF-P), human growth hormone, transferrin, epidermal growth factor (EGF), low density lipoprotein, high density lipoprotein, leptin, VEGF, PDGF, ciliary neurotrophic factor, prolactin, adrenocorticotropic hormone (ACTH), calcitonin, human chorionic gonadotropin, cortisol, estradiol, follicle stimulating hormone (FSH), thyroid-stimulating hormone (TSH), leutinizing hormone (LH), progesterone and testosterone; and (3) other proteins (including (Y-fetoprotein, carcinoembryonic antigen CEA, cancer markers, etc.).

Suitable target analytes include carbohydrates, including but not limited to, markers for breast cancer (CA15-3, CA 549, CA 27.29), mucin-like carcinoma associated antigen (MCA), ovarian cancer (CA125), pancreatic cancer (DE-PAN-2), prostate cancer (PSA), CEA, and colorectal and pancreatic cancer (CA 19, CA 50, CA242).

Other suitable target analytes include metal ions, particularly heavy and/or toxic metals, including but not limited to, aluminum, arsenic, cadmium, selenium, cobalt, copper, chromium, lead, silver and nickel.

In one embodiment, the methods of the invention are used to detect pathogens such as bacteria. In this embodiment, target sequences include rRNA, as is generally described in U.S. Pat. Nos. 4,851,330; 5,288,611; 5,723,597; 6,641,632; 5,738,987; 5,830,654; 5,763,163; 5,738,989; 5,738,988; 5,723,597; 5,714,324; 5,582,975; 5,747,252; 5,567,587; 5,558,990; 5,622,827; 5,514,551; 5,501,951; 5,656,427; 5,352,579; 5,683,870; 5,374,718; 5,292,874; 5,780,219; 5,030,557; and 5,541,308, all of which are expressly incorporated by reference.

In one embodiment nucleic acid sequencing methods are used. Sequencing methods are described in U.S. Ser. No. 09/626,096, filed Jul. 26, 2000, Ser. No. 09/847,113, filed May 1, 2001, Ser. No. 10/137,710, filed Apr. 30, 2002, Ser. No. 10/336,255, filed Jan. 2, 2003 and Ser. No. 10/823,502, filed Apr. 12, 2004, all of which are expressly incorporated herein by reference.

As will be appreciated by those in the art, a large number of analytes may be detected using the present methods; basically, any target analyte for which a binding ligand, described below, may be made may be detected using the methods of the invention. While many of the techniques described below exemplify nucleic acids as the target analyte, those of skill in the art will recognize that other target analytes can be detected using the same systems.

If required, the target analyte is prepared using known techniques. For example, the sample may be treated to lyse the cells, using known lysis buffers, electroporation, etc., with purification and/or amplification as needed, as will be appreciated by those in the art. When the target analyte is a nucleic acid, the target sequence may be amplified as required; suitable amplification techniques are outlined in PCT US99/01705, hereby expressly incorporated by reference. In addition, techniques to increase the amount or rate of hybridization can also be used; see for example WO 99/67425 and U.S. Ser. Nos. 09/440,371 and 60/171,981, all of which are hereby incorporated by reference.

The samples comprising the target analytes can be added to the fluidics devices described herein. By "fluidics device" is meant device comprising a substrate, at least one channel, inlet ports and outlet ports as well as valves. The fluidics device of this disclosure can take on numerous configurations.

By "cartridge" herein is meant a casing or housing for the biochip. As outlined herein, and as will be appreciated by those in the art, the cartridge can take on a number of configurations and can be made of a variety of materials. Suitable materials include, but are not limited to, fiberglass, teflon, ceramics, glass, silicon, mica, plastic (including acrylics, polystyrene and copolymers of styrene and other materials, polypropylene, polyethylene, polybutylene, polycarbonate, polyurethanes, Teflon™, and derivatives thereof, etc.), etc. Particularly preferred cartridge materials are plastic (including polycarbonate and polyproplylene) and glass.

As will be appreciated by those in the art, the cartridge can comprise a number of components, including reaction chambers, inlet and outlet ports, heating elements including thermoelectric components, RF antennae, electromagnetic components, memory chips, sealing components such as gaskets, electronic components including interconnects, multiplexers, processors, etc.

In one embodiment, the cartridge comprises a reaction chamber. Generally, the reaction chamber comprises a space or volume that allows the contacting of the sample to the biochip array. The volume of the reaction chamber can vary depending on the size of the array and the assay being done. In general, reaction chamber ranges from 1 mL to about 1 mL, with from about 1 to about 250 .mu.l being preferred and from about 10 to about 100 .mu.l being especially preferred. In some embodiments, to avoid the introduction of air bubbles into the reaction chamber (which can be disruptive to detection), the reaction chamber is less than the size of the sample to be introduced, to allow a slight overflow and thus ensure that the reaction chamber contains little or no air.

In one embodiment, the biochip cartridge can be configured to include additional chambers that can used for any number of different reactions, such as sample preparation, cell lysis, rare target capture/concentration, sample clean-up, nucleic acid amplification, including PCR, post-amplification clean-up, sample concentration, reagent storage, mixing baffles/devices, etc. In other embodiments, the reaction chamber may be configured for other types of reactions as generally described below.

In one embodiment, the biochip cartridge reaction chamber is configured to include at least one nucleic acid amplification chamber. However, multiple amplification chambers may be used. That is, a cartridge may comprise from about 1 to about 10 or more chambers, with 2, 3, 4, 5, 6, 7, 8 or 9 also being preferred.

In one embodiment, the biochip cartridge reaction chamber is configured to include at least one PCR chamber. However, multiple PCR chambers may be used. That is, a cartridge may comprise from about 1 to about 10 or more chambers, with 2, 3, 4, 5, 6, 7, 8 or 9 also being preferred.

In one embodiment, the chamber of the cartridge should be made from biocompatible materials. In particular, materials that provide a surface that retards the non-specific binding of biomolecules, e.g. a "non sticky" surface, are preferred. For example, when the reaction chamber is used for PCR or amplification reactions a "non sticky" surface prevents enzymatic components of the reaction mixture from sticking to the surface and being unavailable in the reaction. In addition, the biocompatible properties of the chamber may be improved by minimizing the surface area.

Biocompatible materials include, but are not limited to, plastic (including acrylics, polystyrene and copolymers of styrene and other materials, polypropylene, polyethylene, polybutylene, polyimide, polycarbonate, polyurethanes, Teflon™, and derivatives thereof, etc.) Other configurations include combinations of plastic and printed circuit board (PCB; defined below). For example at least one side of the chamber is printed circuit board, while one or more sides of the chamber are made from plastic. In one embodiment, three sides of the chamber are made from plastic and one side is made from printed circuit board. In addition, the chambers, channels, valves, pumps, etc. of the systems described herein may be coated with a variety of materials to reduce non-specific binding. These include proteins such as caseins and albumins (bovine serum albumin, human serum albumin, etc.), parylene, other polymers, etc.

In one embodiment, the reaction chamber of the cartridge comprises an inlet port for the introduction of the sample to be analyzed. Depending on the reaction being run, multiple inlet ports may be used, that may feed from a variety of storage chambers or from the outside of the chamber. The inlet port may optionally comprise a seal to prevent or reduce the evaporation of the sample or reagents from the reaction chamber. In one embodiment, the seal comprises a gasket, or valve through which a pipette or syringe can be pushed. The gasket or valve can be rubber or silicone or other suitable materials, such as materials containing cellulose.

The reaction chamber can be configured in a variety of ways. In one embodiment, the reaction chamber is configured to minimize the introduction or retention of air bubbles or other sample impurities. Thus for example, assuming that the cartridge is held in an upright angle, the inlet port allows the flow of fluid sample into the "bottom" of the reaction chamber, to allow the escape of air or fluid through the "top" of the reaction chamber, for example through an outlet port. Thus the fluid sample flows up into the reaction chamber and contacts the array. Thus, in one embodiment, the reaction chamber further comprises an outlet port to allow air or excess sample to exit the reaction chamber. In some embodiments, the outlet port vents to either a waste storage well, as is further described below, to an external surface of the chip or cartridge, or, in one embodiment, back into the inlet port. Thus for example one embodiment utilizes a system wherein the exit port vents to the inlet port, preferably above the point of loading. For example, when a pipette is used to load the cartridge, the tip of the pipette extends below the exit port, such that air from the exit port is not introduced into the reaction chamber. In addition, the materials of the cartridge housing and biochip can be chosen to be similar in hydrophobicity or hydrophilicity, to avoid the creation of air bubbles.

In one embodiment, an anti-siphon vent is used to prevent liquid from being sucked back into a chamber as a result of the negative pressure generated when an air pump heater is turned off. For example, a anti-siphon vent comprising a paraffin valve and an open port can be constructed between the reaction chamber and an air pump.

In addition, in one embodiment, the reaction chamber/inlet and/or outlet ports optionally include the use of valves. For example, a semi-permeable membrane or filter may be used, that preferentially allows the escape of gas but retains the sample fluid in the chamber. For example, porous teflons such as Gortex™ allow air but not fluids to penetrate.

In one embodiment, a reaction chamber in the biochip cartridge (such as a PCR chamber) has one or more valves controlling the flow of fluids into and out of the chamber. The number of valves in the cartridge depends on the number of channels and chambers. Alternatively, the biochip cartridge is designed to include one or more loading ports or valves that can be closed off or sealed after the sample is loaded. It is also possible to have multiple loading ports into a single chamber; for example, a first port is used to load sample and a second port is used to add reagents. In these embodiments, the biochip cartridge may have a vent. The vent can be configured in a variety of ways. In some embodiments, the vent can be a separate port, optionally with a valve, that leads out of the reaction chamber. Alternatively, the vent may be a loop structure that vents liquid and/or air back into the inlet port.

As will be appreciated by those in the art, a variety of different valves may be used. Microvalves can be categorized into two major types: passive microvalves (without actuation) and active microvalves (with an actuation). Generally, active microvalves couple a flexible diaphragm to a thermopneumatic, piezoelectric, electrostatic, electromagnetic, bimetallic actuator. Additional valves find use in the invention and are described in more detail in US Pub. No. 2007/0098600 which is expressly incorporated herein by reference for disclosure describing valves.

Accordingly, in a first aspect, the invention features a fluidics device, preferably multilaminate, having a diaphragm and a plurality of check valves contiguous with said diaphragm through one or more flow channels. The diaphragm is acted upon by a pump, which in one embodiment is extraneous to the device itself but nevertheless engageably interfaceable therewith. In one embodiment the check valves are passive "bridge" valves as described herein, which essentially comprise more or less parallel slits in a flexible laminate sheet which can allow displacement of the section therebetween upon application of force, thereby routing fluid flow along a new path, in one embodiment, in a direction more or less parallel to the laminate portion flanking the slits. In one embodiment the system is pump or vacuum-driven.

By "multilaminate" is meant prepared from multiple, e.g. more than one, layers. Polyethyleneterepthalate (PET) and etched polytetrafluoroethylene (PTFE) find particular use as construction materials, but other materials as discussed herein can also be used, with the overall multilaminate comprising a single material or multiple different materials. In general, as described herein, at least 2, 3, 4, 5 or more layers are used, as is shown in the figures. Generally, one or more of the layers have vias, e.g. shaped holes therein, such that when sandwiched between two additional layers (e.g. a "top" and a "bottom") they form the channels of the chips as described herein. Similarly, one of the layers generally includes the array of electrodes (which as outlined herein can be within a detection chamber as a rectilinear array, within a detection chamber comprising a serpentine (or other geometries) channel, etc.), which is laminated to a layer defining a channel. As described herein, the layers may be attached in a wide variety of ways, including adhesives (pressure sensitive, heat sensitive, etc.). In addition, as outlined herein, the individual layers can also contain features for attachment, like posts or pegs that couple to corresponding holes in another layer.

By "diaphragm" is meant a flexible seal that flexes in a positive and negative fashion. In one embodiment the diaphragm is positioned in a first chamber or separates multiple chambers. In one embodiment the diaphragm is within an enclosed system. Thus, upon movement of the diaphragm ni a positive or negative direction, either air or materials within the enclosed system move in response to the movement of the diaphragm. In one embodiment the diaphragm includes a magnet. This allows for movement of the diaphragm by controlling movement of the magnet, which can be accomplished electrically.

By "flow channels" is meant a channel through which a liquid flows in the cartridge of this disclosure. The dimensions of the flow channel are significant in that the linear speed of the fluid over the electrodes is dependent on the channel cross section. Additionally, the channel height and width must be great enough to allow any bubbles to freely flow through the channel and eventually be trapped/cleared in the reservoir. Therefore, it is important to design a channel that is small enough to provide sufficient linear velocity but not too restrictive with respect to bubble movement. Another consideration is that the lower channel dimensions will utilize less analyte solution, often a desired characteristic. Channel widths of may be from 0.020-0.100", more preferably, 0.025-0.080" and more preferably from 0.030-0.060". Channel heights may be from 0.002-0.020", more preferably from 0.004-0.015" and more preferably from 0.006-0.015". For example, channel widths 0.030-0.060" and heights of 0.006"-0.014" were tested as compatible ranges, with the preferred dimensions being a width of 0.040" and height of 0.010".

Valves are described above. In one embodiment the check valve is a "bridge valve" as described herein. In some embodiments, the bridge valves are contained in the same laminar piece or layered composite as the diaphragm.

In one embodiment the diaphragm is in a first chamber such as a reaction chamber and a second chamber such as a detection chamber may be separate. In some embodiments channels connect the first and second chambers as described herein. Alternatively, the channel itself is used for detection. 1 In this embodiment the detection chamber or the channel, when it is used for detection, includes ligands for binding target analytes as described herein. Also as described herein the ligands may form an array on a substrate in the detection chamber or channel.

The channels are preferably defined by two or more laminate layers and preferably elongated, most preferably serpentine. Preferably, inside the channel are surfaces containing affixed ligand(s), which in turn abstract or bind specific complement, anti-ligand or analyte from a fluid sample that is pumped through the channel and across those surfaces. Preferably the abstracting surfaces are configured in a dimension that does not waste surface area space, the effect of which is to conserve volume and sensitivity per sample volume, and thereby allow for or facilitate miniaturization.

There are two primary means by which fluid can be moved in the biochip cartridge. These are: (1) through the use of a pump that pushes the fluid in or out; or, (2) by suction that pulls fluid in or out of the chamber.

Generally, a device such as a moving piston is used to create suction, however cooling of gases, vacuum chambers and gas consuming reactions can be used. When suction is used to move liquid in or out of the chamber, a vacuum may be created elsewhere in the system.

In some embodiment the pump can be on the chip or off the chip. By "on chip" is meant that the pump is integral to the cartridge itself by "off chip" is meant that the chip is separate from and not integral to the chip. Basically, two major groups of pumps, classified based on different pump mechanisms (i.e., actuation), can be use in the present invention: membrane actuated (i.e., mechanical) and non-membrane actuated pumps. Membrane actuated pumps can be further divided into three types: piezoelectric, electrostatic, and thermopneumatic. Non-membrane pumping principles include electrohydrodynamic, electroosmotic, traveling wave, diffuser, bubble, surface wetting, rotary, etc.

In one embodiment, an "air pump" is used to move the liquid out of the PCR chamber. In this embodiment, a chamber of air is incorporated in the chip with an "on chip" heater. When the heater is turned on, the air in the chamber expands according to PV=nRT. In some embodiments, the air pump is incorporated into the cartridge.

Preferably, heaters (as are also described below) are incorporated into the middle of the chip. In some embodiments, more than one heater is incorporated in a chip to create "heater zones". Air chambers or pockets are located over the heater zones. The air chambers are connected to the reaction chamber via a channel that runs up to the top of the reaction chamber with a valve or a plug blocking it off. When the air is heated, it expands. The resulting build up in pressure forces the valve or plug to move out of the way, thereby forcing the liquid out of the chamber via an outlet port.

Other ways of moving liquid out of the reaction chamber or reaction chamber include using a low boiling liquid in place of air. In this embodiment, the low boiling liquid expands when heated and displaces the liquid contained in the reaction chamber. Alternatively, a chemical reaction may be used to move liquid out of the reaction chamber. For example, the chemical reaction used to expand car air bags may be used to move liquid out of the reaction chamber, or other reactions in which gases are generated.

Other types of pumps that can be used include syringe driven pumps. These pumps can be actuated either by expanding air behind the syringe or by mechanical means. For example, TiNi alloys, nitinol wire, or "shape memory metals" can be used to mechanically actuate a syringe driven pump. By "TiNi alloys", "nitinol wire" or "shape memory metals" herein is meant materials that when heated above a certain transition temperature contract (i.e., usually up to 3 to 5% over the original length of the metal), thereby changing shape. Other materials that change shape upon heating include shape memory plastics.

Pumps also may be created using spring loaded pistons. In this embodiment, a spring that can be released is compressed or restrained within the body of the cartridge. For example, wax may be used to hold a spring in its compressed state. Upon heating, the wax is melted, and the spring is released, thereby generating sufficient force to move a piston and displace liquid. Other versions include incorporating materials that change from solids to liquids at a given transition temperature, or moving a mechanical blockade from the spring's pathway.

Pumps that utilize PZT driven actuations are also known and may be incorporated int this invention. By "PZT" herein is meant a material comprised of lead, zirconium and titanium which upon application of a voltage undergoes a rearrangement of the crystal lattice and generates a force and a displacement. This so called piezoelectric effect can be used to constrict and expand a pump chamber and result in a net movement of liquid. Other materials like shape memory alloys that under a change in shape upon application of a current such that the temperature of the metal is raised above a certain transition temperature can also be used.

In addition, commercially available micro pumps may be used in to move liquid from one location to another in the cartridge. Examples of commercially available pumps include, moulded plastic micro pumps available from IMM (see liganews@imm.uni-mainz.de), thin film shape alloy microactuators (TiNi Alloy Company, San Leandro, Calif.), silicon micro pumps (see M. Richter & J. Kruckow, aktorik/paper/2000jahresbericht/Paper2, 16.11.00).

In addition, based on the geometry of the chamber, air can be used to push liquid out of the reaction chamber or mix liquids within the reaction chamber. Whether the air pumps the fluid or bubbles through to generate a mixing effect is determine by the relative size of the bubble, the geometry of the chamber/channel and the surface tension of the liquid. Larger air-liquid interfaces tend to favor mixing over pumping. Mixing of liquid within the biochip cartridge can occur by pumping the liquid back and forth in the biochip cartridge.

In one embodiment, flow-induced mixing is used to induce convectional flow. Preferably, this is used in a vertical system, such that fluid gravity may be used to induce convectional flow. The convectional flow results in bulk fluid mixing between two liquid solutions. In addition, meniscus recirculation mixing can be used to induce circulation flow (Anderson, et al., (1998) Solid-State Sensor and Actuator Workship, Hilton Head Island, June 9-11, pp 7-10; incorporated herein by reference in its entirety).

In one embodiment, mixing is accomplished by creating a thermal gradient across a chip. For example, a thermal gradient may be created by heating the bottom of the chip to 65° C. and cooling the top of the cartridge cover to 10° C. This can be accomplished by placing the chip between two peltier heaters, or by using an imbedded heater and a single peltier or other thermoelectric cooling devices.

In one embodiment, mixing is accomplished by recirculating liquid in a given chamber using an on chip or "off chip" pump attached to a chip.

In alternative embodiments, mixing is accomplished by recirculating liquid using a micro disk-pump, such as a plastic disk embedded with a magnetic steel bar. Rotation of the disk pump may be achieved using an external magnetic filed provided by a standard stirrer or custom built with multiple fields. See also U.S. Ser. No. 60/308,169, filed Jul. 26, 2001 and a provisional application by Gallagher, et al., entitled "System and methods for mixing within a microfluidic chamber", filed Jul. 11, 2002; both of which are incorporated by reference in their entirety.

In other embodiments, biochannel based mixing can be used to enhance hybridization rates. In this embodiment, a bubble is intentionally introduced into one corner of the chip. By alternately expanding and contracting the bubble volume via the application of heat from either an in chip or off chip heat source, mixing occurs as a result of the pressure flow created by changing the volume of the bubble within the chip. Alternatively, resonance induced mixing of bubbles can be done using PZT devices as well.

In some embodiments, mixing may be accomplished using non-contact mixing technologies like that describe by Covaris, Inc.

In one embodiment, heaters are incorporated onto or into the chip, to allow "on chip" heating (in addition, as described below, "off chip" thermocontrollers within the device may also be used). In this embodiment, the reaction chamber is designed to maximize thermal conductivity between the chamber and the heater or thermocontroller. Generally, designs that minimize thermal mass (i.e., making the surface of the chamber in contact with the heat source as thin as possible), impose certain geometric constraints to ensure the complete removal of liquid from the chamber, incorporate materials that are good thermal conductors (i.e., metals), and thermally isolate the chamber from the rest of the chip are preferred. Often one makes a trade off between minimizing surface to volume ratios to reduce surface area for the non-specific binding of biological components and maximizing surface-to-volume ratios in order to obtain rapid heat transfer rates for heating and cooling.

In one embodiment, air pockets or vents are used to thermally isolate the amplification chamber from the rest of the chip. That is, the there is a break in the continuity of the cartridge around the amplification chamber.

Figure 10:
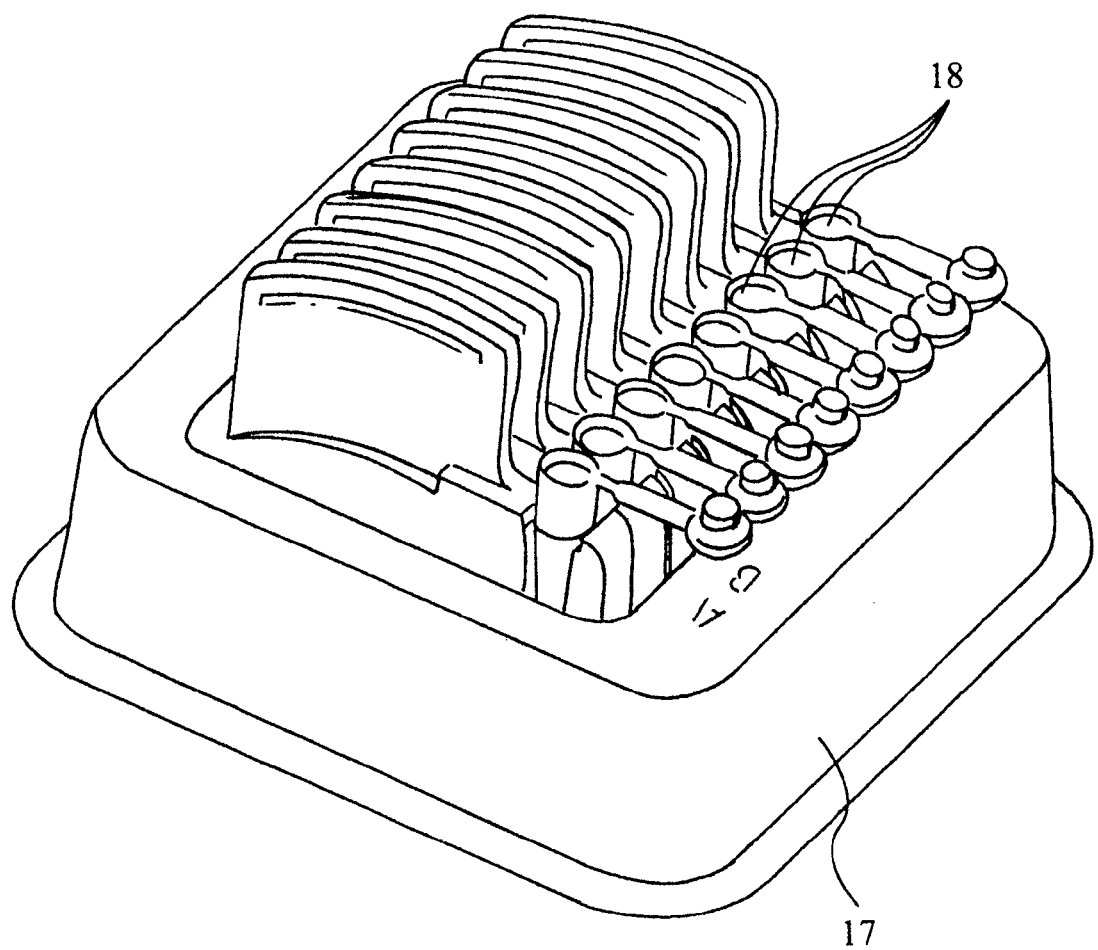
FIG. 10 is a perspective view of a rack containing multiple cartridges vertically aligned and stacked, with sample fill reservoirs facing upward for receipt of liquid samples from a liquid delivery system, such as a multi-pipetteman.
Figure 11:
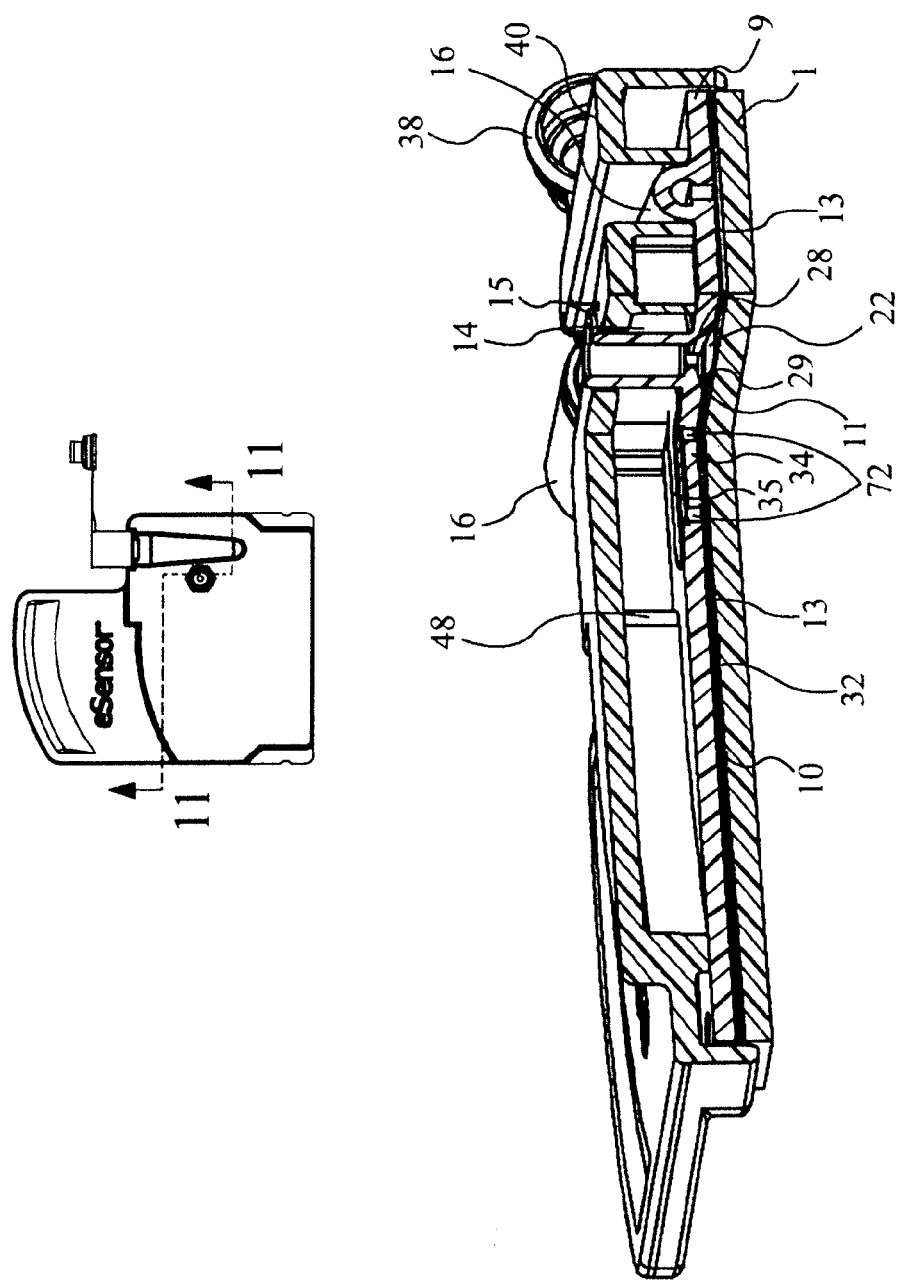
FIG. 11 is a sectional view of a fully assembled cassette embodiment, showing cooperativity of the PCB board, laminate assembly, plate, and cover to afford fluidic operation. Shown are the channels, valving, diaphragm and pneumatic pump interface.
Figure 12:
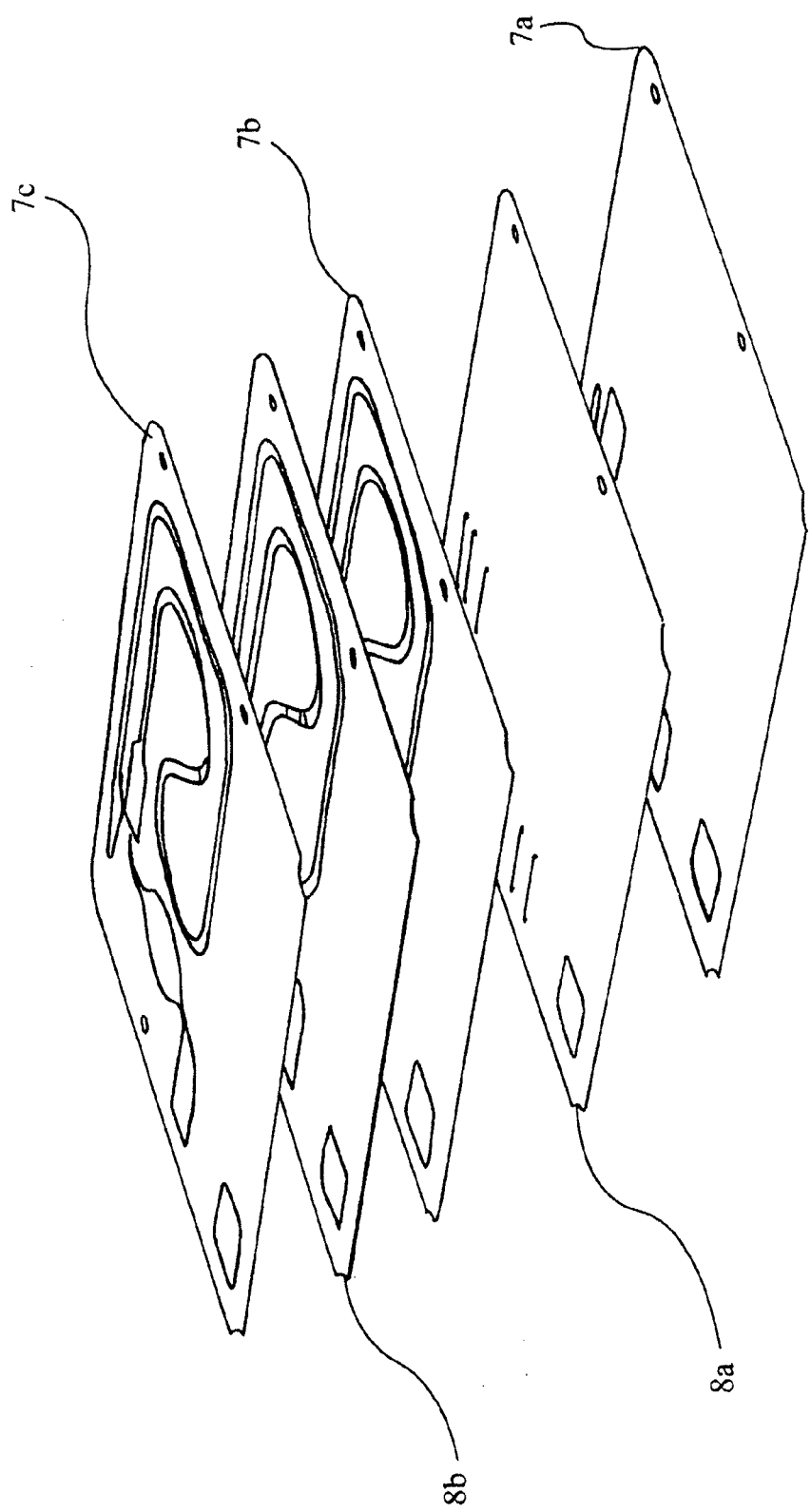
FIG. 12 is similar to FIG. 8, showing an exploded view of the individual laminate and adhesive layers comprising the laminate assembly.

In one embodiment, thermally conductive materials are incorporated into or below the reaction chamber, forming hybrid chambers. For example, by using "layers" of different materials, effective heaters are constructed. Thus for example, one embodiment utilizes one or more resistive heaters in the form of resistive metallic inks can be applied to a first layer of PC board. These heaters are powered by interconnects. In one embodiment, a thin sheet of a thermally conductive material, preferably a metal such as copper, is applied, to allow even heat distribution. In one embodiment, the copper layer is then coated with a thin layer of biocompatible material, such as plastic. See FIG. 10A.

The total thickness of the hybrid chamber may vary from a few microns to millimeter dimension. A preferred thickness is approximately 200 microns.

In one embodiment, multiple thermal heaters are incorporated into the device to allow for the creation of multiple thermal zones. The temperature in the respective zones is maintained via either active or passive control. Frequently, the thermal connectivity of the cartridge materials are taken into account during the design. In one embodiment, a chip may contain a thermal heater in the detection chamber of the cartridge in order to maintain the temperature of the detection chamber as well as constructing unique temperature zones in another part of device. In one embodiments, these temperature zones may be maintained to allow an enzymatic reaction to run efficiently. In another embodiment, multiple temperature zones may be maintained to simulate the temperatures normally used during PCR heat cycling. In order to effect the necessary temperature, the liquid can be maintained stationary and the temperature of the amplification chamber cycled (i.e. 95-55-72), alternatively, the liquid can be pumped over different temperature zones in order to obtain heat cycling. This embodiment can be realized in different material substrates such as glass, plastic, ceramic and PCB.

Similarly, there may be portions of the substrate that require heating, and those that do not. Thus more than one heater may be incorporated into the substrate. Similarly, these thermal zones may or may not be thermally isolated from other parts of the substrate. For example, PC board is significantly thermally insulative, and thus just putting distance between the heaters and thermal zones and the areas of the substrate that do not require heating may be sufficient. In other embodiments, thermally insulative materials may be incorporated. For example, when the substrate is a ceramic material, thermal isolation may be accomplished by cutting out sections of the ceramic substrate such that solid regions of ceramic are separated from one another by a "cut out".

Other embodiments include the incorporation of temperature sensors into the substrate such that the temperature throughout the board can be monitored. In one embodiment, temperature sensors are created using resistive devices, including silicon diodes. Other embodiments include the use of capillary thermostats and limiters, such as those offered by Thermodisc.

As will be appreciated by those in the art, there are a variety of reaction chamber geometries which can be used in this way. Generally having the intersection of the inlet port and the reaction chamber be at the "bottom" of the cartridge, with a small aperture, with the reaction chamber widening, is preferred. In addition, the "top" of the reaction chamber may narrow, as well. Thus, preferred embodiments for the size and shape of the reaction chamber allow for smooth loading of the reaction chamber. Preferred embodiments utilize reaction chamber geometries that avoid the use of sharp corners or other components that serve as points for bubble formation.

In addition, in some embodiments, the reaction chamber can be configured to allow mixing of the sample. For example, when a sample and a reagent are introduced simultaneously or separately into the chamber, the inlet port and/or the reaction chamber can comprise weirs, channels or other components to maximize the mixing of the sample and reagent. In addition, as is outlined below, the reaction may utilize magnetic beads for mixing and/or separation.

In one embodiment, the cartridge comprises a sealing and/or venting mechanism to prevent the cartridge from exploding due to a build up in pressure during a reaction, or to prevent leakage of the sample or reagents onto other parts of the substrate, particularly (in the case of electronic detection) onto electronic interconnects. As will be appreciated by those in the art, this may take on a variety of different forms. In one embodiment, there is a gasket between the biochip substrate comprising the array and the cartridge, comprising sheets, tubes or strips. Alternatively, there may be a rubber or silicone strip or tube used; for example, the housing may comprise an indentation or channel into which the gasket fits, and then the housing, gasket and chip are clamped together. Furthermore, adhesives can be used to attach the gasket to the cartridge, for example, a double sided adhesive can be used; for example, silicone, acrylic and combination adhesives can be used to attach the gasket to the biochip, which is then clamped into the cartridge as described herein.

In embodiments where the surfaces are electrodes, each electrode surface preferably occupies a majority of the channel width and is positioned in series relative to other electrodes, with a channel height thereover that allows fluid to flow thereacross through the channel.

In some embodiments, the individual laminate pieces are substantially planar and "stack" to thereby form the multilaminate device and internal features in operable form. In other embodiments, the individual laminate pieces are substantially nonplanar or modular, and still cooperatively stack or interface, e.g., like Ruffles® or Pringles® potato chips.

In a second aspect, the invention features a method of constructing a multilaminate fluidics device by mating/conjoining the individual laminate pieces noted above. This is preferably accomplished by stacking and fusing or otherwise sealing the individual pieces together to thereby form a device having one or more functional chambers, channels, diaphragms and/or valves, etc. therein.

In yet a third aspect, the invention features a method of using a multilaminate fluidics device as above by adding a fluid sample thereto and interfacing with a pump mechanism (e.g., syringe pneumatic, hydraulic, thermal, or electromechanical) and magnetic, electronic, or other detection device (e.g., colorimetric, electrochemical, isotopic, densitometric, etc.), and prectifying flow through the device so that the sample can be acted upon or analyzed, e.g., by a laser or detector in one or more downstream channels or chambers.

In some embodiments, flow is preferably of a two-stroke design wherein the diaphragm is periodically moved back and forth or up and down to actuate/rectify directional fluid flow across cooperating tandem valves having the diaphragm fluidly coupled therebetween. In operation, one valve is substantially closed when the other is substantially open, depending on stroke, and vice-versa.

In some embodiments the device is a disposable one, and reversibly engageable with a pump and/or electronic stimulation or detection component that can be used over and over again, e.g., a laser and/or an optical, voltametric, amperometric, and/or thermal reader.

In some embodiments, the device is used for in vitro diagnostics.

In some embodiments, the device is used with or has integrated a filtration, purification, separation, and/or mixing means as known in the art.

In a fourth aspect the invention features a single laminar sheet bearing one or more of a diaphragm, valving, and/or channels. This sheet can be a component of the first aspect. In embodiments, the sheet is formed of either PET, polypropylene, ultra high molecular weight polyethylene, low density polyethylene, high density polyethylene, linear low density polyethylene and/or Teflon®, and is preferably 5 mm or less in thickness, more preferably 2 mm or less in thickness, and most preferably 1 mm or less in thickness. These sheets may be present as part of a large roll of individual sheets of identical or complementary dimension. The sheets may be individually machined, molded, stamped, chemically-etched and/or laser ablated to carry the individual features noted. The individual sheets may also be perforated or otherwise rendered separable from the roll to be thereafter incorporated into a larger multilaminate fluidics device according to the invention. One can readily envision an automated or semi-automated procedure whereby a uniform roll of laminate undergoes stamping, machining, molding, etching, welding and/or ablation to endow microfluidics features in a volume batching format using standard methodologies and capabilities known in the art.

In a fifth aspect the invention features a device having inlet and outlet ports that are joined to effectively re-circulate sample while simultaneously facilitating gas removal and thereby facilitating molecular diffusion and efficiency of the microfluidic system. This aspect can be combined with any of the preceding aspects and embodiments as appropriate, e.g., by suitable injection molding, machining, stamping, etching, ablation, and mated sealing of individual laminates using adhesives, gaskets, clamps, solvent bonding, ultrasonic welding, etc. Preferably, gas removal is accomplished by circulating the fluid sample past a bubble trap or enclosed gaseous environment located above the fluid flow path.

In some embodiments, the multilaminate device processes (or are designed to process) no more than 1 mL of fluid/analyte sample at a time. In some other embodiments, no more than 150 uL of fluid is processed at a time. In still others, preferably no more than about 100 uL or less is processed at a time.

In multilaminate embodiments, the individual pieces may optionally be held together and sealed by pressure sealing adhesive sheets, welding, and/or using conformable gasket-like material such as silicone or silicone sheeting.

In some embodiments, one or more channels or chambers are formed by grooves, cuts or recesses in one or more of the cooperating laminate sheets, e.g., as provided by a die-stamp, chemical etching or laser ablation technique, as those techniques are commonly understood in the art.

In some embodiments, biological binding partners such as proteins, peptides, antibodies, nucleic acid and polynucleotides/oligonucleotides are preferably attached to surfaces in the system, e.g., on electrodes, which are preferably contained in some of the channels or chambers that receive the liquid samples upon flow through the device. Preferably those samples are recirculated, which improves binding efficiency and result by simultaneously augmenting diffusion and effecting mixing, washing and shear strain to overcome problems associated with laminar flow.

A continuous flow rate of about 10-40 uL/sec in connection with the dimensions used herein has been found to be optimal, but pulsed flow is also envisioned to work. These principles need not be tied to multilaminate devices alone, but can be adopted for any device and with like effect.

Preferred attachment means for the binding partners are by adsorption or self assembling monolayer derivatization and addition/spotting to/of the surfaces on which they are affixed, e.g., electrode(s).

In some embodiments, the devices are preferably made of a transparent or translucent material that permits visualization of the circulation and recirculation of fluid sample.

In some embodiments, syringes or pneumatic pumps or other means may drive the system, which may or may not be electromechanical in nature.

In some embodiments, the individual cartridges are "stacked" and oriented such that a set pitch exists between individual inlet sample ports in neighboring cartridges. This allows for convenient use of multi-well pipetting devices and the like to load samples. A common pitch in the industry for this is ~9 mm.

In some embodiments, channels are wider than tall. In some embodiments, channel dimensions range from about 0.030" to about 0.060" in width and 0.006" to about 0.014" in height.

In some alternating laminate and adhesive layer embodiments, individual layer thicknesses range of from about 0.0005" to about 0.010". In some preferred embodiments, laminate layers are thicker than adhesive layers. In some embodiments, laminate layers range from about 0.0005" to about 0.030" thickness and adhesive layers from about 0.001" to about 0.003" thickness.

By "substantially parallel" is meant not perpendicular to one another.

Other aspects and embodiments will be apparent to one of ordinary skill in the art from the background documents, drawings, detailed description, and claims to follow.

The individual aspects and embodiments of the invention can be combined as appropriate in any combination. Advantages from the combinations include, as appropriate for a given aspect/embodiment: lower cost, ease of fabrication and mass fabrication, ease of reproducibility, improved flow, improved mixing, and elimination or minimization of gaseous bubble formation that would otherwise obstruct sample flow, and facilitated analyte diffusion and electrolyte conductivity.

Ease of Use

As the diagnostic testing environment becomes more decentralized (from large central labs to smaller hospital labs, to patient bedsides, and into the field), highly-trained and specialized operators become more scarce. Ease of use is a key criterion for successful implementation in such an environment. This invention includes several features that address this need.

One way to make a system easier to use is to incorporate more "intelligence", which is most effective when software is provided with useful information. Incorporating inexpensive information storage into the cartridge in a format that can be read from and written to is quite advantageous. Barcodes are an example of media that provide read-only storage that may transfer information from the cartridge manufacturer to the instrument, e.g. identification of what test protocol should be run or what the cartridge expiration date is. Read-only systems used in conjunction with instrument databases further allow the association of fixed identification information (e.g. a cartridge serial number) with data unknowable at manufacture (such as the specific locale and instrument used for testing, the testing status, and the reported results). Media such as EEPROMs and some RFID formats have the added ability to write to the cartridge, which allows independence from a database and permits any instrument to retrieve the information without requiring networked access to a central server. (An "EEPROM" is short for Electronically Erasable Programmable Read-Only Memory, which is a non-volatile storage chip used in computers and other devices to store small amounts of volatile (configuration) data. EEPROMs come in a range of capacities from a few bytes to over 128 kilobytes and are typically used to store configuration parameters, and in modern computers they replace the hitherto common CMOS nonvolatile BIOS memory).

Another way to drive ease of use is to make a system fully compatible with preexisting technologies for sample handling. For example, liquid samples in labs are commonly transferred using volumetric pipettes. While there is some degree of standardization, variations in available tip geometries could make compatibility with a custom interface difficult. However, given that these pipettes have been designed to transfer fluids into microcentrifuge tubes and microtiter plates, any cartridge with a sample input reservoir that mimics these other systems will be at an advantage.

Further advantage can be gained through compatibility with standard parallel processing and automation equipment. Manual multipipettes and robotic pipetting systems are generally designed to interface with a standard 96-well microtiter plate format, i.e. with tips separated by a 9 mm pitch and in arrangements of 8×12 (or a subset of this array). This makes cartridges that can nest together at a 9 mm pitch especially advantageous.

Yet further ease of use can be achieved by making customer interaction with the physical cartridge simple and obvious, especially when troubleshooting. For example, transparency is a valuable though often overlooked feature. A transparent sample input reservoir allows the operator to confirm that the sample has been added to the cartridge, and a graduated reservoir allows confirmation that the necessary volume has been added. A transparent fluid path allows operators to see if there has been a problem with fluid handling or with bubbles.

Analyte Capture

While ease of use is important for broad acceptance by consumers, the keystone of a diagnostic system is its detection technology. In one broad class of such technologies, the specific binding of an analyte to an immobilized partner (commonly affixed to a surface) is the prelude to an observable signal. The rate at which such a capture event occurs is generally proportional to the concentration of analyte present at that surface.

As the analyte molecules nearest to the surface bind, the local analyte concentration becomes depleted. This can slow the capture of subsequent molecules, reducing the sensitivity of the system and the time-to-answer, so efforts to replenish the analyte can reap rewards. For example, quickly flowing the analyte-containing fluid over the capture site shrinks the boundary layer that bulk analyte molecules must diffuse across in order to be captured. In cases of extreme depletion, such fluid motion also carries new, "un-accessed" fractions of the sample nearer to the capture region.

There are many possible configurations for flowing a fluid across a surface. While not the only workable geometry, one convenient arrangement is to flow the analyte fluid through a channel over the capture site. In this layout the constricted cross section increases the flow velocity for a given volume transferred, and several capture surfaces can be placed sequentially along the channel to experience a more or less equivalent flow profile.

Actuating the motion of fluid through this channel can also be done in many different ways. For a rectified flow, one configuration comprises inserting a pump at one end of the system, or one in the middle with a check valve on each side. Oscillating flow likely needs no valving but might require a compression chamber if in a linear rather than cyclical configuration.

One advantage to rectified flow that could justify its additional complexity can be seen when considering bubbles, an additional impediment to analyte capture. If a capture surface is stored dry, it is possible to generate bubbles of trapped air as the sample is introduced. Outgassing from the cartridge materials is also possible, and outgassing from the sample is virtually guaranteed given that the mixing techniques commonly used to prepare samples will also aerate them. In each of these scenarios, bubbles might reduce how effectively an analyte is captured. However, the ability to strip bubbles from the system can mitigate the issue. In a system with rectified flow, a bubble-stripping chamber can be inserted into the fluid path.

For example, consider a design that could make use of the bubbles' buoyancy to extract them. Create a holding reservoir with an inlet that adds fluid near the top and an outlet that removes it from the bottom. (Note that "top" and "bottom" do have a critical meaning in this context because buoyancy is only meaningful in gravity or a similar mass acceleration field.) Some reserve of standing fluid is present in the reservoir. When new fluid with bubbles enters from the top, the bubbles float on the top of this reserve until they collapse, while the new fluid mingles with the other liquid. Fluid is pulled from the bottom of this standing liquid to refresh the system.

It is important to design the system so that there is always standing liquid at the bottom of the reservoir, otherwise air or un-collapsed bubbles will get pulled from the chamber into the rest of the system and defeat the purpose. (For example, there needs to be at least enough liquid to accommodate any pulsing nature of the fluid propulsion.) However, there does not necessarily need to be any dead air space at the top of the reservoir for this bubble-stripping chamber to work. The chamber just needs to have a geometry such that the force due to the fluid flow pulling the liquid into the drain is less than the buoyancy force propelling the bubbles away from the drain.

Electrochemical Detection

After an analyte has been captured, this binding event must be converted into a signal that is observable by a detection instrument. One way is to use electrochemistry to convert the chemical binding event into an electrical current. In this embodiment, the capture surface must also be an electrode.

Electrochemical detection can have several advantages over alternative methods, but it has its own special requirements. Electrochemical techniques call for the creation of an electrochemical cell, often a three-electrode cell where there is a working electrode (the sensor surface) linked through a conductive electrolyte solution to an auxiliary electrode (a current source/sink) and a reference electrode (a voltage reference). Any disruption in this conductive link can impact the electrochemical scan, so the bubble stripping described for analyte capture is just as important for electrochemical detection. The use of redundant auxiliary electrodes is an additional way to reduce the risk of a break in conductivity: the path to each auxiliary electrode would have to be blocked in order to compromise the electrochemical circuit.

Of course, electrical connectivity with the instrument is just as important as electrical connectivity through the electrolyte solution. Given the paradigm that many disposable cartridges will be interfacing with a non-disposable piece of equipment, that equipment's connector must be robust to many cycles. Furthermore that connector should be able to create many connections in order to enable the analysis of many different working electrodes from one cartridge. A zero insertion force (ZIF) connector with a two-dimensional grid of contacts is one good solution.

The following commonly owned or controlled patents describe electrochemical detection principles and methodologies in more detail: U.S. Pat. Nos. 5,591,578, 5,824,473, 6,177,250, 6,277,576, 6,268,149, 6,268,150, 6,180,352, 6,200,761 6,238,870, 6,258,545, 6,528,266, 5,770,369, 6,096,273, 7,014,992, 6,221,583, 6,090,933, 7,045,285, 6,479,240, 6,977,151, 7,125,668, 6,265,155, 6,291,188, 7,033,760, 6,232,062, 6,495,323, 7,056,669, 6,013,459, 6,013,170, 6,248,229, 7,018,523, 6,740,518, 6,063,573, 6,600,026, 7,160,678, 6,290,839, 6,264,825, 6,761,816, 7,087,148, 6,541,617, 6,942,771, 6,432,723, 6,833,267, 7,090,804, 6,686,150, 5,620,850, 6,197,515, 6,322,979, 6,306,584, 7,172,897, 6,753,143, 6,518,024, 6,544,734, 6,642,046, 6,592,696, 6,572,830, 6,361,958, 6,960,467, 6,602,400, 6,824,669, 6,596,483, and 6,875,619, all of which are incorporated herein by reference for their disclosure related to detection principles and methodologies.

Specific ligand attachment chemistries, including self-assembling monolayer technology, is also discussed in detail in U.S. Pat. Nos. 6,306,584, 5,620,850, 6,472,148, 6,197,515, 6,322,979, 6,809,196, 5,620,850, 6,197,515, 6,322,979, and 6,306,584, all of which are expressly incorporated herein by reference for disclosure related to ligand attachment chemistries, including self-assembling monolayer technology (for example when the electrodes of the invention comprise self-assembled monolayers (SAMs)). The compositions of these SAMs will vary with the detection method used. In general, there are two basic detection mechanisms. In one embodiment, detection of an ETM is based on electron transfer through the stacked ni-orbitals of double stranded nucleic acid. This basic mechanism is described in U.S. Pat. Nos. 5,591,578, 5,770,369, 5,705,348, and PCT US97/20014 and is termed "mechanism-1" herein. Briefly, previous work has shown that electron transfer can proceed rapidly through the stacked n-orbitals of double stranded nucleic acid, and significantly more slowly through single-stranded nucleic acid. Accordingly, this can serve as the basis of an assay. Thus, by adding ETMs (either covalently to one of the strands or non-covalently to the hybridization complex through the use of hybridization indicators, described below) to a nucleic acid that is attached to a detection electrode via a conductive oligomer, electron transfer between the ETM and the electrode, through the nucleic acid and conductive oligomer, may be detected.

Alternatively, the ETM can be detected, not necessarily via electron transfer through nucleic acid, but rather can be directly detected on an electrode comprising a SAM; that is, the electrons from the ETMs need not travel through the stacked n orbitals in order to generate a signal. As above, in this embodiment, the detection electrode preferably comprises a self-assembled monolayer (SAM) that serves to shield the electrode from redox-active species in the sample. In this embodiment, the presence of ETMs on the surface of a SAM, that has been formulated to comprise slight "defects" (sometimes referred to herein as "microconduits", "nanoconduits" or "electroconduits") can be directly detected. This basic idea is termed "mechanism-2" herein. Essentially, the electroconduits allow particular ETMs access to the surface. Without being bound by theory, it should be noted that the configuration of the electroconduit depends in part on the ETM chosen. For example, the use of relatively hydrophobic ETMs allows the use of hydrophobic electroconduit forming species, which effectively exclude hydrophilic or charged ETMs. Similarly, the use of more hydrophilic or charged species in the SAM may serve to exclude hydrophobic ETMs.

The person of ordinary skill in the art will appreciate that electrochemical detection may be accomplished in a variety of ways to detect a variety of different analytes. Osmetech's eSensor® DNA Detection Technology is illustrative of one way of detecting nucleic acid sequences.

The eSensor® microarray is composed of a printed circuit board (PCB) consisting of an array of gold electrodes that are each modified with a multi-component, self-assembled monolayer (SAM) that includes pre-synthesized oligonucleotide capture probes. Nucleic acid detection is based on a sandwich assay principle. Signal and capture probes are designed with sequences complementary to immediately adjacent regions on the corresponding target DNA sequence. A three-member complex is formed between capture probe, target, and signal probe based on sequence-specific hybridization, which brings the 5'-end of the signal probe containing electrochemically-active ferrocene labels into close proximity with the electrode surface. The ferrous ion within each ferrocene group undergoes cyclic oxidation and reduction, leading to loss or gain of an electron, which is measured as current at the electrode surface using alternating current voltammetry (ACV) and higher-order harmonic signal analysis. The ferrocene labels are only detected when the signal probe is captured at the surface of the electrode by sequence-specific hybridization. In the absence of target, no specific signal is detected.

Osmetech's current system is adapted to specifically detect genetic mutations and polymorphisms by employing allele-specific signal probes containing ferrocene labels with distinguishable redox potentials. The signal probe matching the wild-type sequence contains a ferrocene label of one electrochemical potential, and a second signal probe matching the mutant sequence contains a second, distinguishable ferrocene label. Both the wild-type and mutant targets bind to the capture probe at a site adjacent to the mutation. The wild-type and mutant signal probes then compete for binding to their complementary sequences. The probe with the perfect match to the target is bound with a high degree of preference. The genotype is then determined by the ratio of signals generated by the bound wild-type and mutant signal probes. Genotyping boundaries are established based on statistical analysis of data from a large number of samples, and subsequent identification of unknown samples requires no further calibration of the instrument or cartridge lot. This approach can be used to discriminate single- or multiple-base changes, insertions and deletions. A mutation site with multiple alleles, or two adjacent mutation sites, can be genotyped using additional ferrocene labels.

Superior Cartridge/Instrument Interface

Regardless of the chosen analytical method, the interface between cartridge and instrument must be designed for reliability and ease-of-use. For example, appropriate alignment between the cartridge and the fluid flow actuation must be ensured, keying features should be added to prevent an operator from inserting a cartridge in the wrong orientation, and protective features may need to be added to prevent damage to the instrument if an inappropriate cartridge interface is forced. In addition, there should be tactile (and/or perhaps audible) feedback to the operator to communicate to them that a cartridge has been inserted correctly. Common detent methods such as spring-loaded balls or compressible lever latches will serve this purpose.

It is also important to be forward-looking when designing the cartridge/instrument interface. Under the "disposable cartridge with reusable instrument" paradigm, new cartridges are frequently shipped to customers to be used with a device already installed in the field. Design choices can be made with that instrument's cartridge interface such that it will be possible to upgrade cartridge design without triggering modification of the instruments themselves. For example, in one embodiment a pressure plate may press against the cartridge in intimate physical contact (to clamp that cartridge into place). However, if the pressure plate were to be designed to conform perfectly with the cartridge's natural design, then no other physical changes to the cartridge shape will be possible in the future without retrofit. However, if a mechanical adaptor is integrated into the cartridge so that a more generic surface is presented to the pressure plate, then future cartridge designs are free to change internal shape with a corresponding adjustment to the adaptor space within, the outside of the cartridge remaining substantially the same.

It should be noted that one or more of the above-noted preferred features may not apply for a given application or embodiment, as the person of ordinary skill in the art will appreciate.

EXAMPLES

Example 1

Cartridge Design & Manufacture

Figure 6:
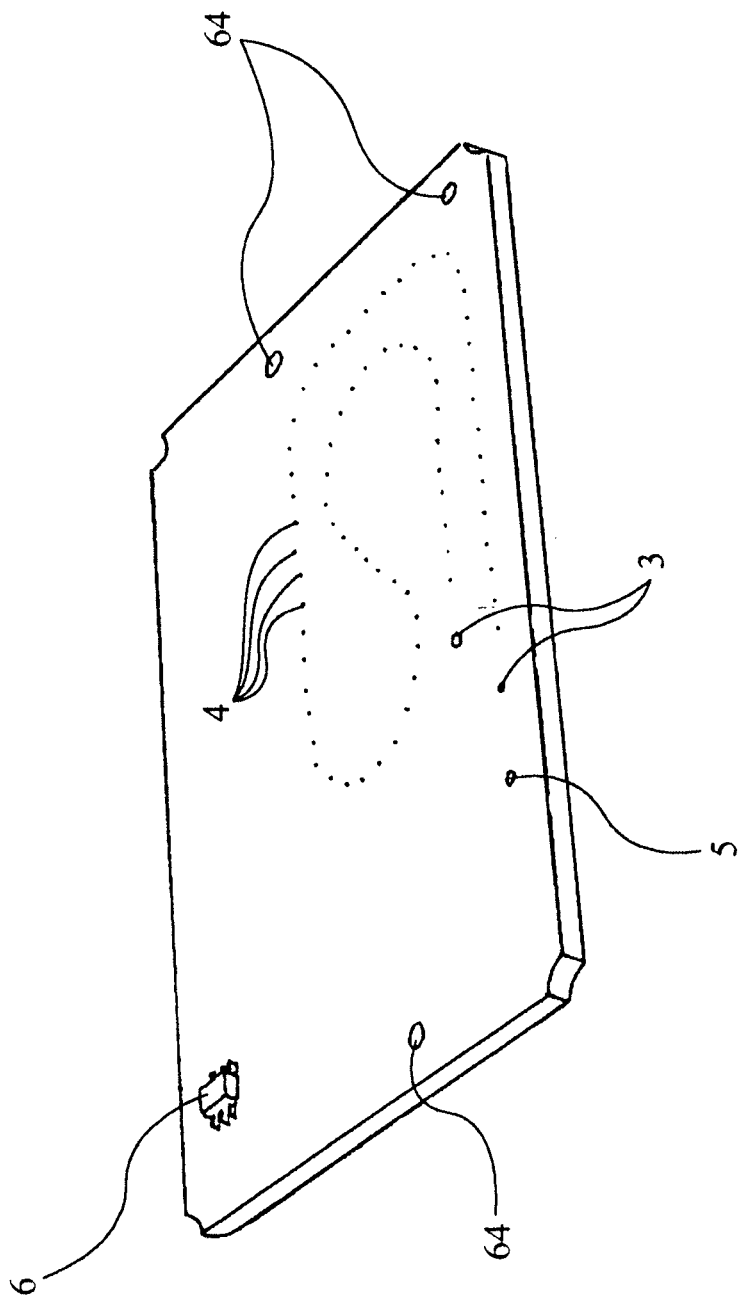
FIG. 6 is a perspective view of a PCB board configured with reference, auxiliary and working electrodes in serpentine configuration, alignment holes and EEPROM. Not visible are the traces and vias linking the individual electrodes to a two-dimensional array of gold contact points on the underside of the PCB board.

With reference to FIG. 6, we have chosen a printed circuit board (PCB) (1) to provide the gold surfaces for a 3-electrode electrochemical cell controlled by a potentiostat circuit. It has dual auxiliary electrodes (3) shorted to one another, a multiplicity of working electrodes (4), and a reference electrode (5). The reference electrode is coated with the same electrically conductive silver material (epoxy) that is used to attach an EEPROM (6), and this silver on the reference is electrochemically oxidized immediately prior to analysis to generate the necessary Ag/AgCl redox couple. (While a more standard solder could have been used to attach the EEPROM, this would have introduced additional chemical compounds and manufacturing steps). The PCB geometry lays the working electrodes in 3D wells, which simplifies the process of applying differing chemical treatments to each electrode to create the desired capture surfaces.

In embodiment, the cartridge device consists of a PCB chip, a cover, and a microfluidic component. The microfluidic component is composed of a plate and a multilayer laminate. The PCB chip includes 72 gold-plated working electrodes (that is twice density of the CFCD chip), a silver/silver chloride reference electrode, and two gold-plated auxiliary electrodes. Each working electrode has its own connector contact pad on the opposite side of the chip to allow electrical connection to an instrument. The entire surface of PCB is coated with an insulating solder mask, leaving only the center (250 mm diameter) of the electrodes exposed. The PCB chip also contains an EEPROM (Electrically Erasable-Programmable Read-Only Memory) component, a memory device that stores information related to the cartridge, such as assay protocol, cartridge lot number, and expiration date.

With reference to FIGS. 1B, 2, 3, 4 and 5, a laminate assembly (2) is affixed on top of the PCB (1), which assembly combines individual layers of pressure-sensitive adhesive (7a-c) and thin plastic laminate layers (8a,b). On top of the laminate assembly is a molded polycarbonate plate (9). The laminate layers define the fluid channel (10) and provide a diaphragm (11) (for interface with a pump) and two check valves. The polycarbonate plate (9) provides the rigid chimney (14), the extreme end of which constitutes the pump interface (15), and also contains a fill reservoir/sample chamber (16) that in this embodiment serves double duty as a bubble-stripping chamber, but that in other embodiments may be a separate chamber/port. All of this is created in a thin enough arrangement to allow cartridges to be held side-by-side in a loading rack (17) with their reservoir openings (18) offset by a 9 mm standard multipipette tip pitch or distance between individual cartridge chambers. For loading rack, see FIG. 10.

Figure 1B:
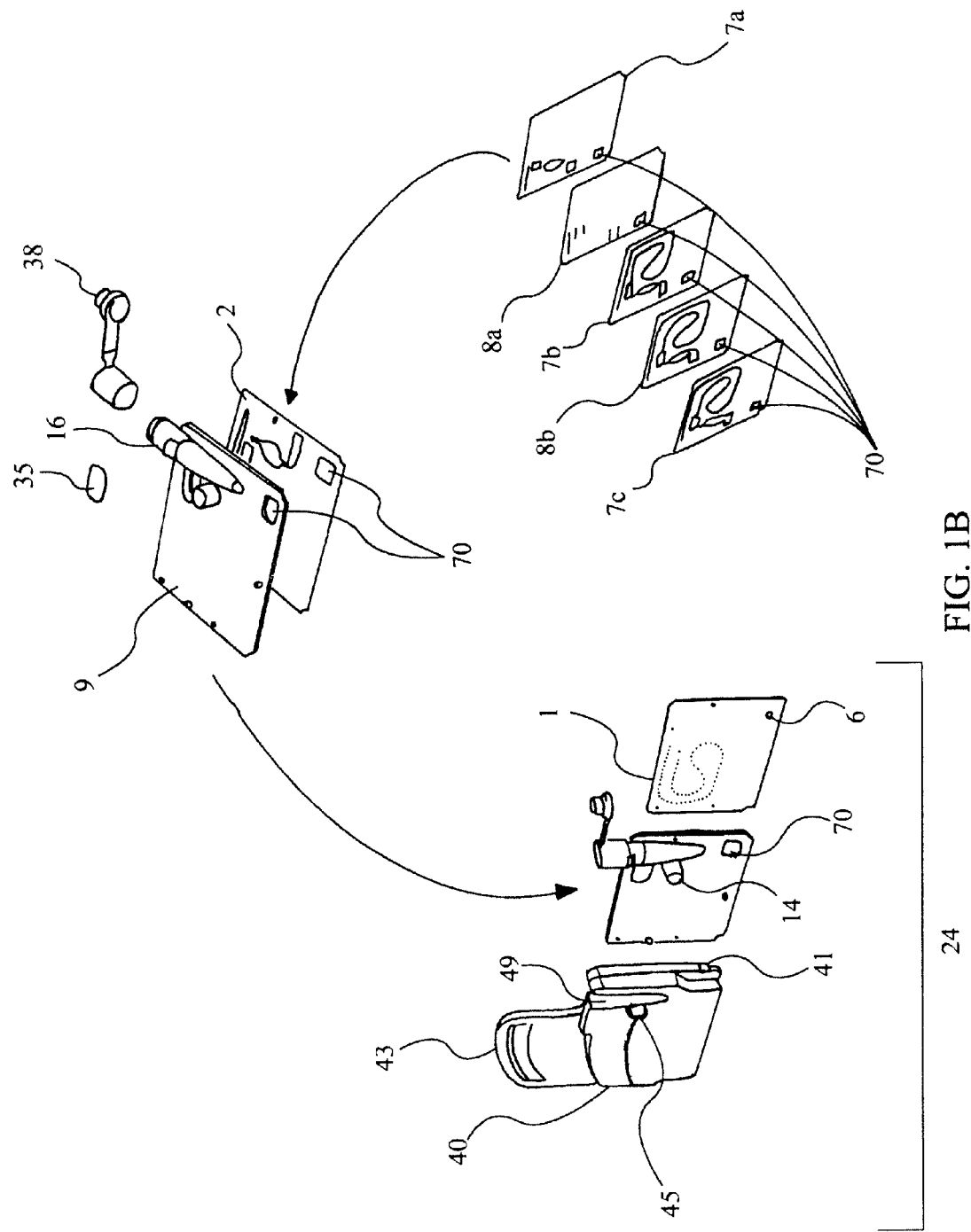
FIG. 1B is an exploded view of the individual components within the cartridge.
Figure 2:
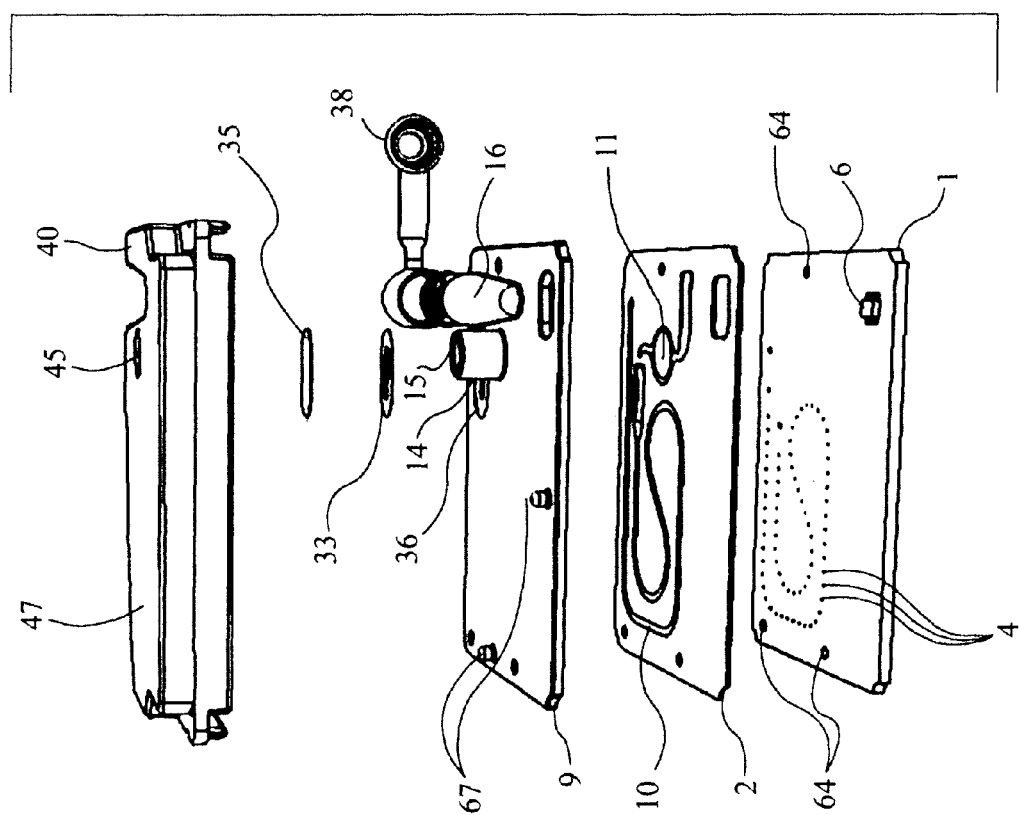
FIG. 2 is another exploded view of FIG. 1 showing PCB (printed circuit board), valve/diaphragm laminate assembly, plate, cover and cap, with visible sample addition fill reservoir, serpentine channel, pump interface, bridge valves, and serpentine electrode array on PCB board configured to interface with serpentine channel in laminate assembly to thereby create one or more fluid channels.
Figure 3:
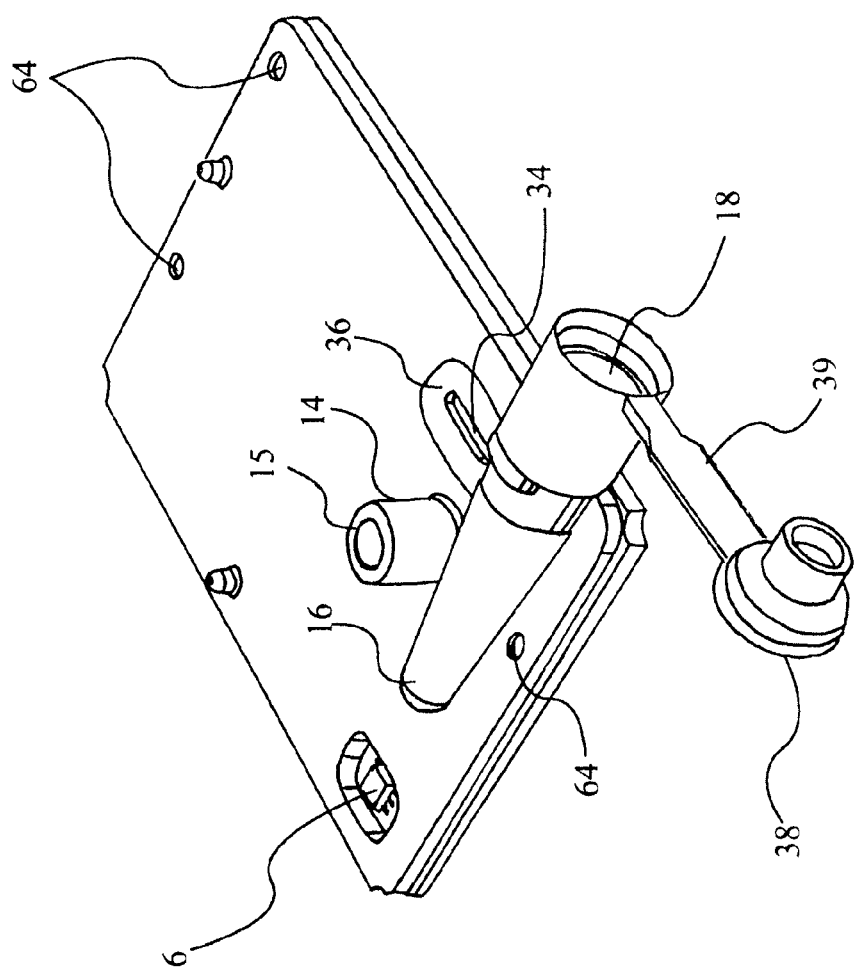
FIG. 3 is a perspective view of a partially assembled cartridge embodiment (less cover) containing pump interface, sample fill chamber/reservoir (with cap), alignment holes, and EEPROM.
Figure 4:
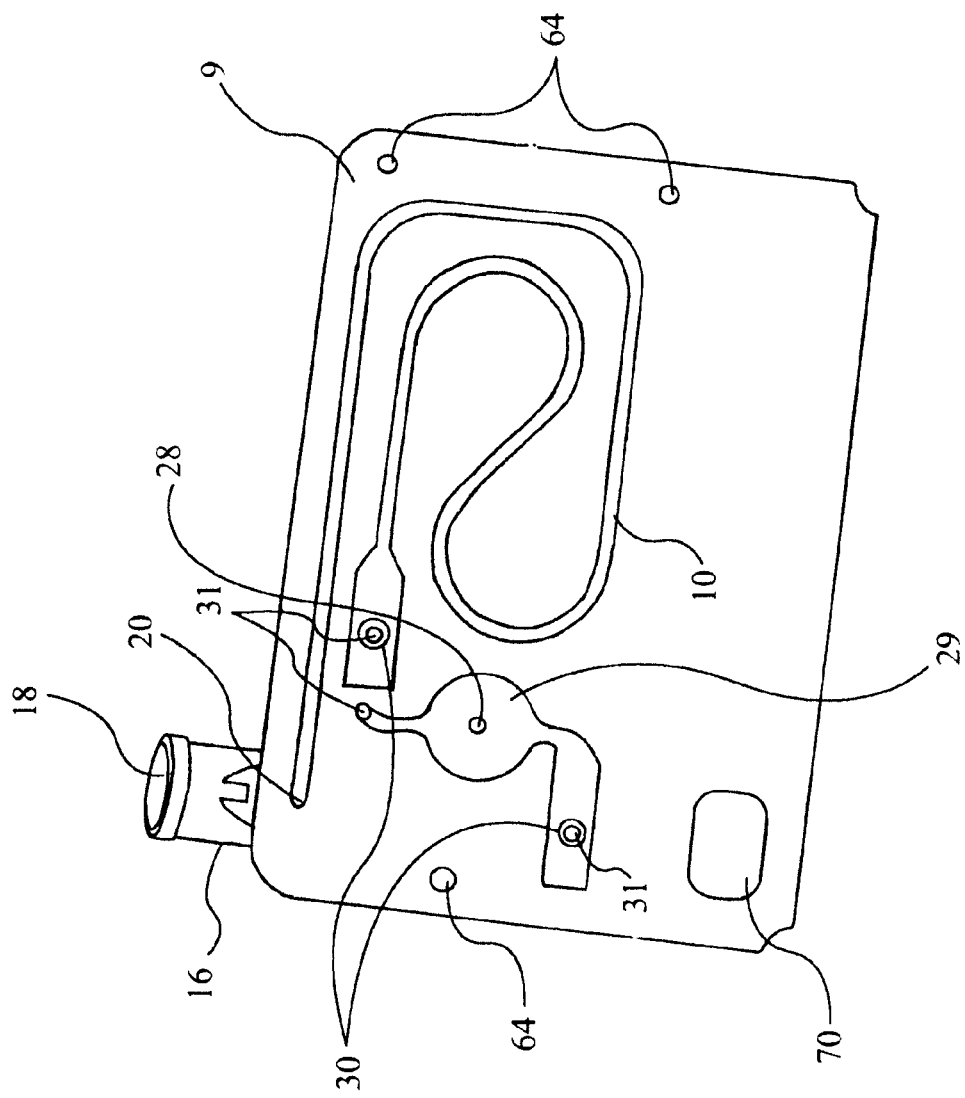
FIG. 4 is a bottom perspective view of a cartridge plate assembly embodiment (less cover, cap and PCB), including alignment holes, void for receiving EEPROM, sample fill reservoir, sample inlet port, and sample outlet port. Also shown are two valve seats, one at the fill reservoir outlet and the second below the ports of the oval recess (above and to the right of diaphragm), a bubble stripping/fill reservoir, and diaphragm for interface with pump.
Figure 5:
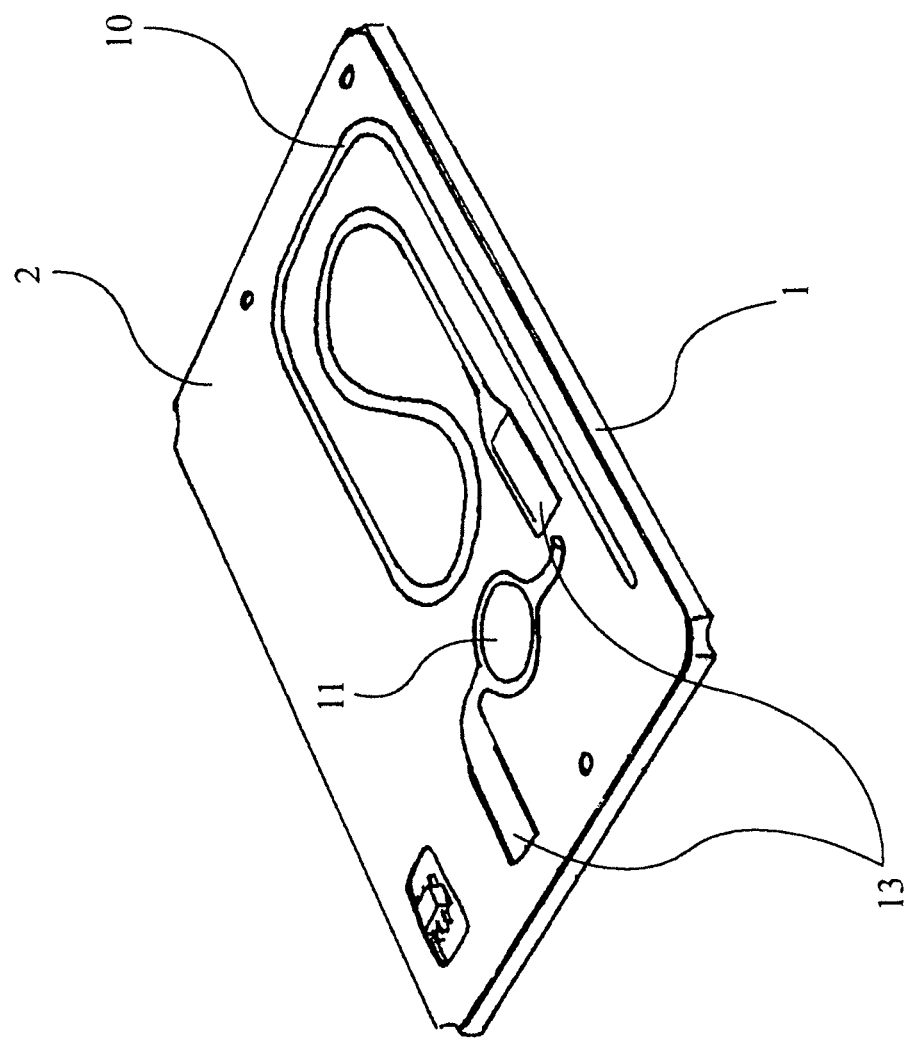
FIG. 5 is a perspective view of a partially assembled cartridge that contains the laminate assembly overlaying the PCB board and that better shows the operational relation between bridge valves, diaphragm, and channel.

With reference to FIGS. 1B, 4 and 5, the walls of the fluid channel (10) are defined by one or more layers (7, 8) of the laminate assembly (2), and are sealed to the PCB (1) by an adhesive layer. While clamping the parts together might be sufficient in some systems, the adhesive provides a more reliable seal, especially for low viscosity solutions. (Although the conductive electrolyte solution necessary for electrochemical detection is usually water-based, the specific additional salts, detergents, or non-aqueous solvents required by the individual chemistries of diagnostic technologies can have a significant impact on the fluid's surface tension and capillary behavior.)

An adhesive layer can also seal the walls of the channel to its ceiling, which can be flat, beveled or otherwise. In one embodiment, the ceiling is formed from a plastic layer comprising a facing of the laminate or conforming channel within the laminate. This allows the laminate part to hold its shape during manufacture. Cutting the channel entirely through to the polycarbonate plate could make the laminate prone to stretching, twisting, or distortion when handled, depending on the geometry of the channel path. For this reason, in certain embodiments, certain of the laminate layers are only partially cut into or sculpted, and not completely so, with other functionalities or complementing features provided by other layers so that no one layer is too weak for practical manufacturing. In other embodiments, the ceiling is provided by the polycarbonate plate/cover.

With reference to FIGS. 2, 4, 5, and 11, rectified fluid flow through the channel (10) is actuated by a diaphragm (11) flanked by two bridge beams (13). The diaphragm (11) is formed from the same layer of plastic laminate that creates the channel ceiling, covering an area where the channel widens into a circular region. However, while the channel ceiling is attached to the polycarbonate plate (9) with a layer of adhesive, the diaphragm (11) is free to oscillate. A local absence of adhesive and a recess/beveled underside (29) in the plate gives the diaphragm (11) freedom to flex toward and away from the PCB (1) surface and form a diaphragm chamber (22). See FIG. 11.

Figure 13A:
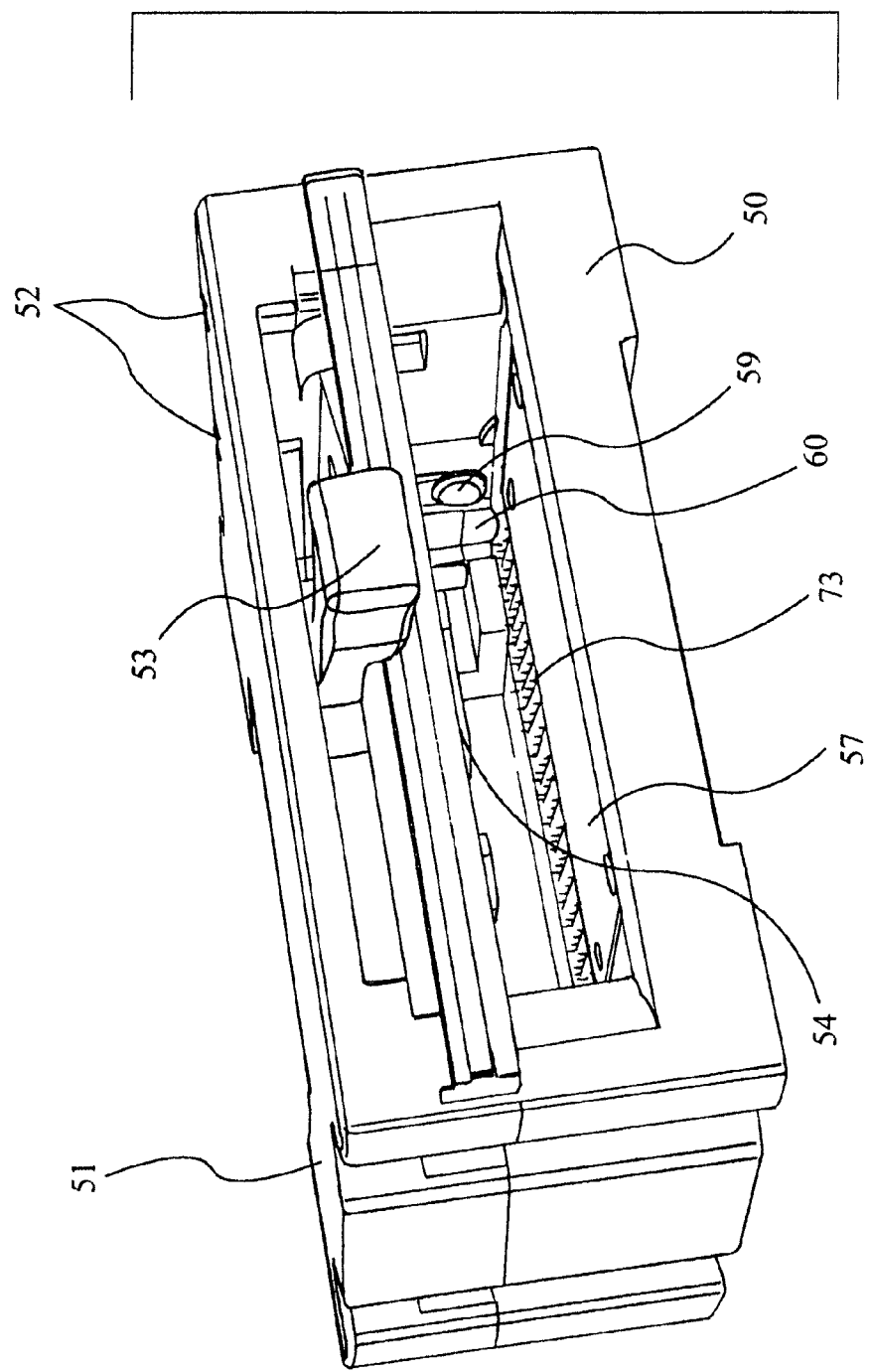
FIG. 13A shows an assembled cartridge module and FIGS. 13B and C respectively show the bottom and top hemispheres of the module, including internal components and design.
Figure 13B:
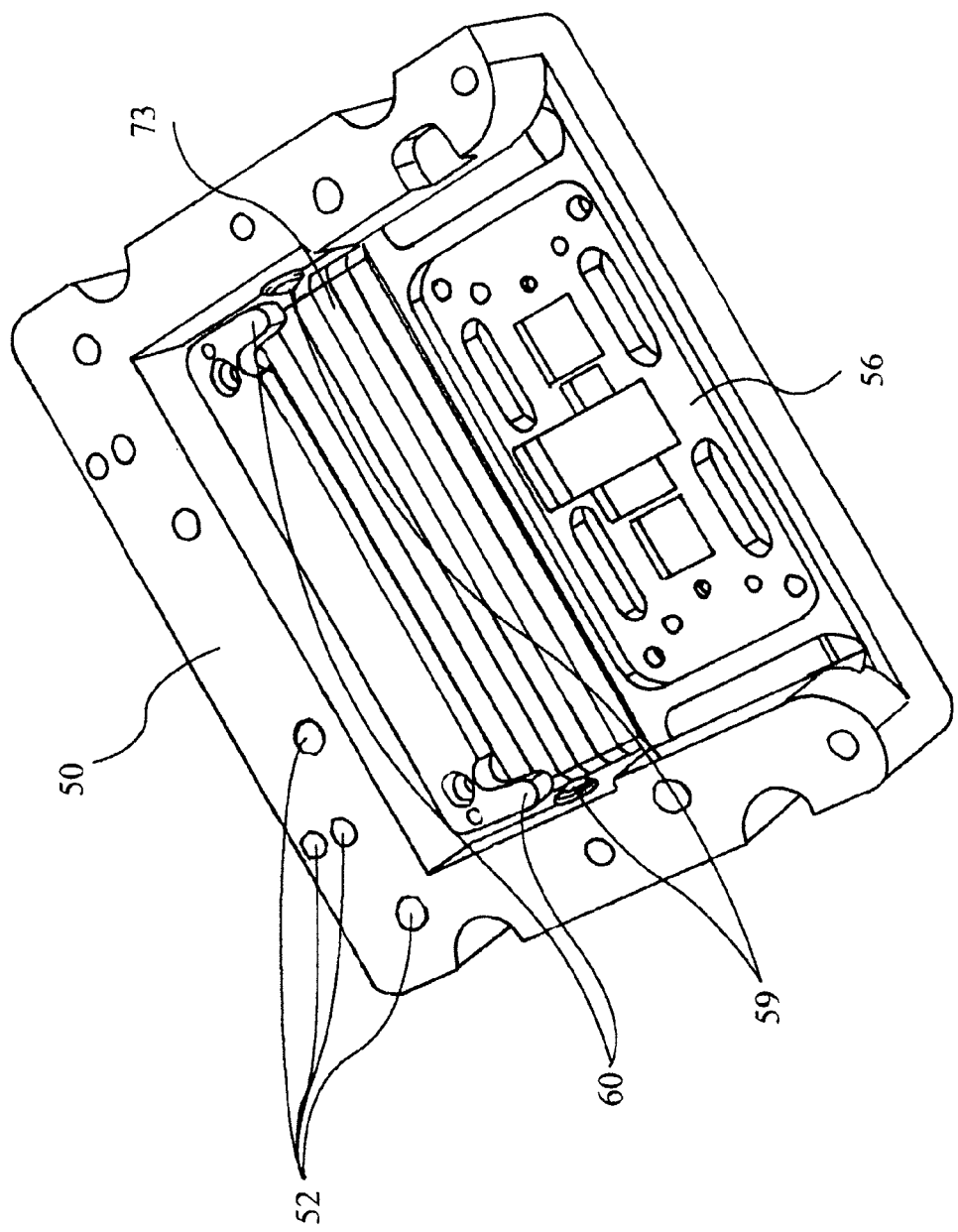
FIG. 13D shows the buckle beam assembly, with one bracket displaced showing buckle beams.
FIG. 13E is a perspective view of the top of the module showing connection to pump.
Figure 13C:
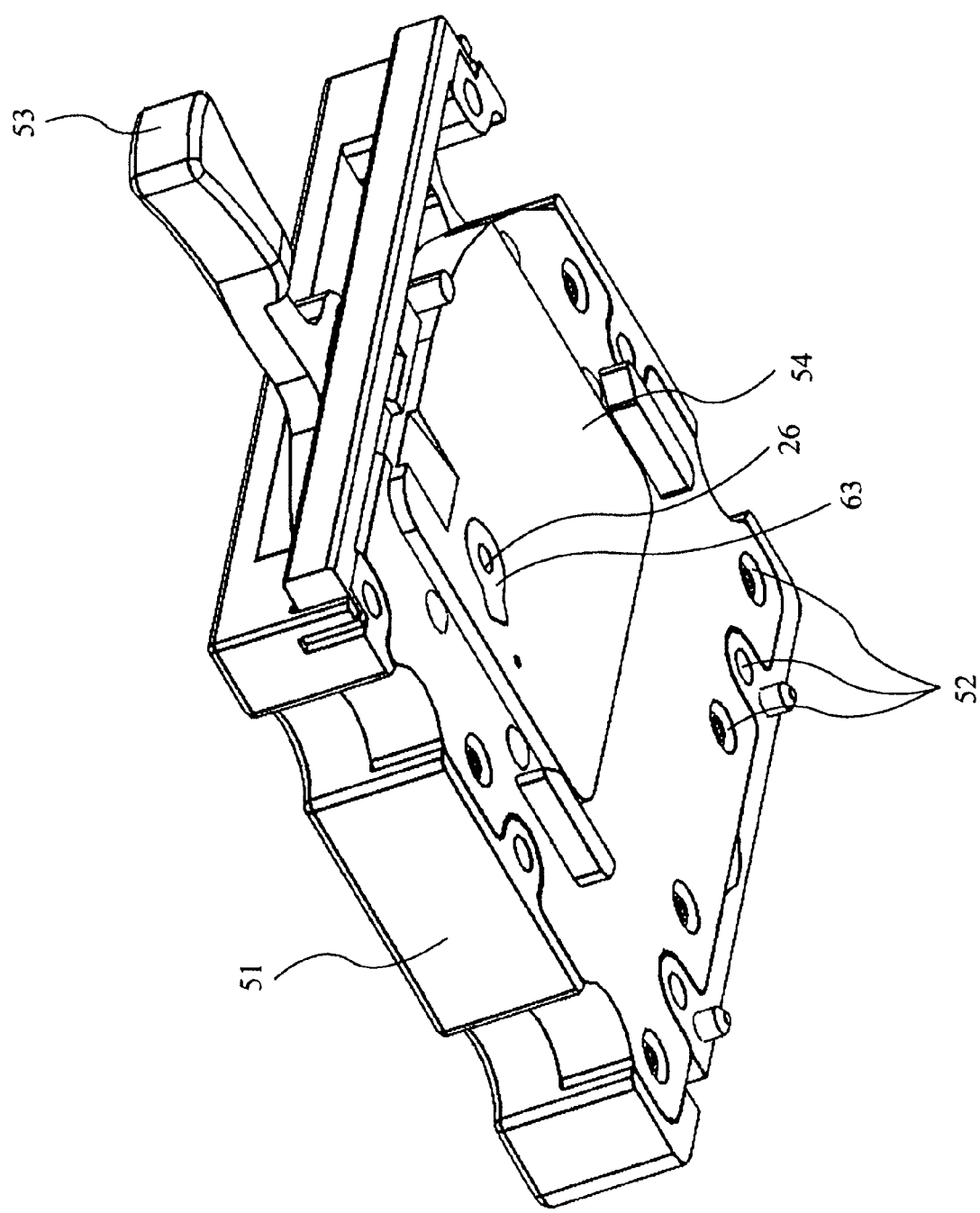
Figure 13D:
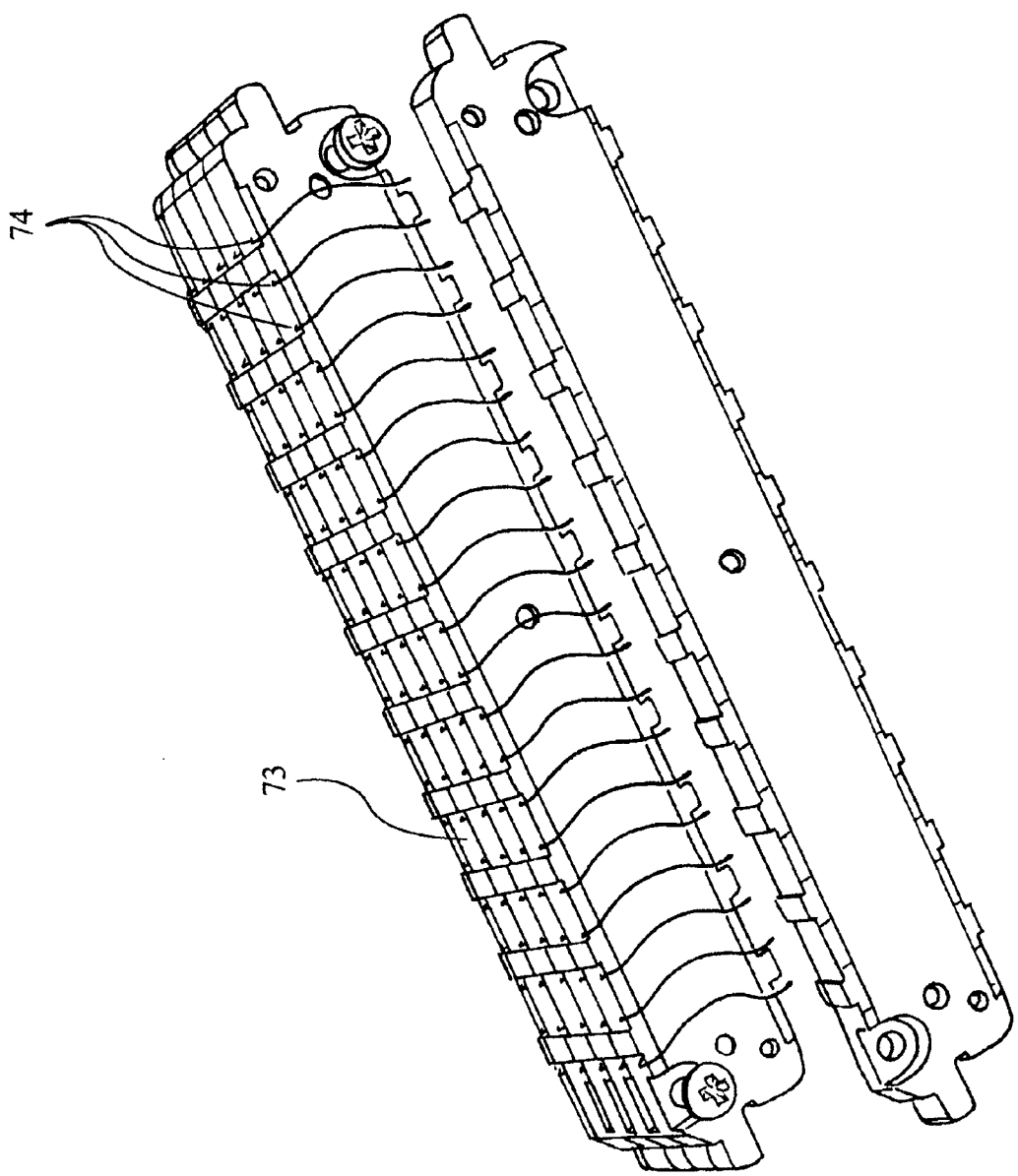
Figure 13E:
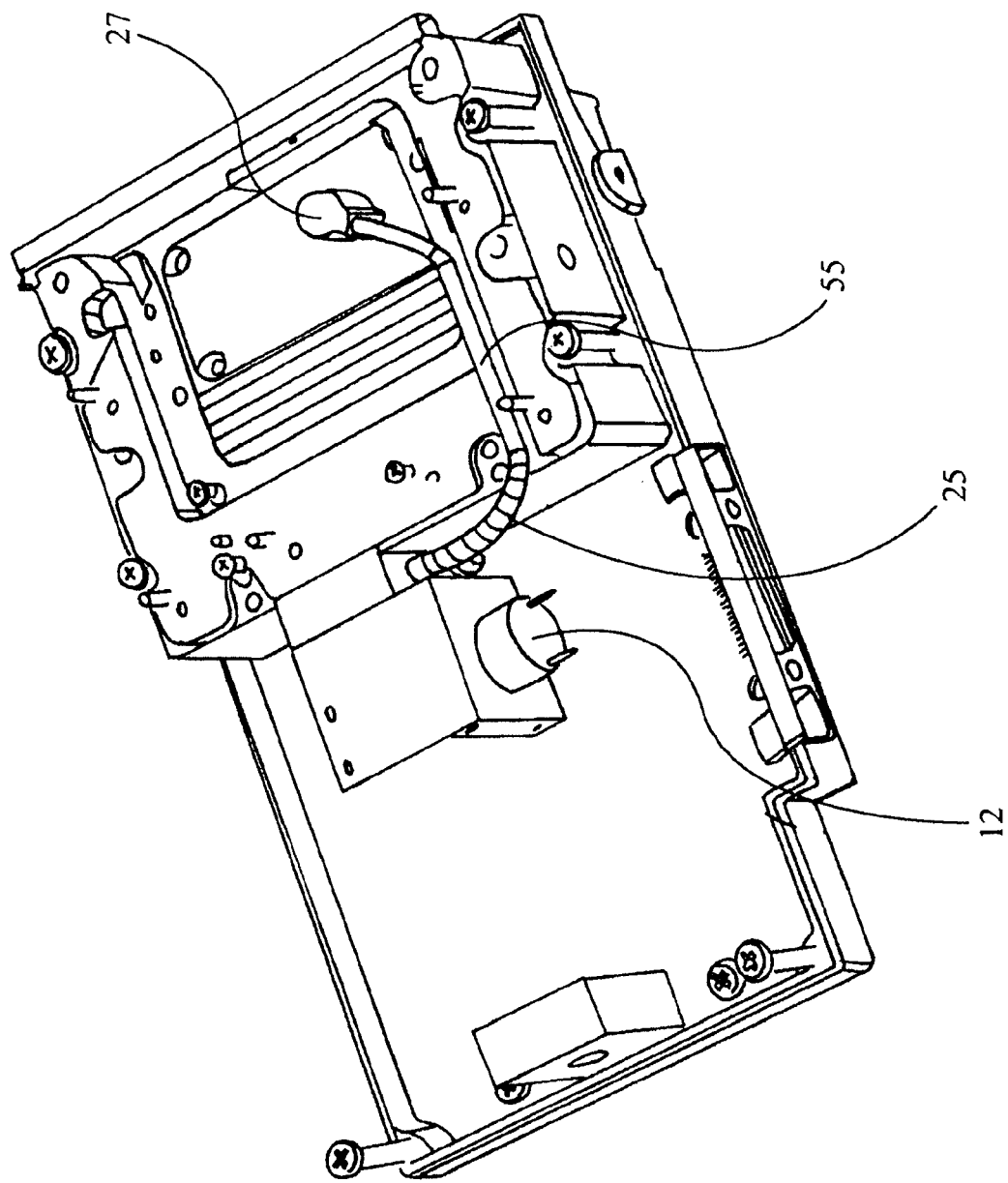

In one embodiment, the cartridge diaphragm (11) is driven by a pneumatic pump (12), preferably one integrated into or alongside a detection instrument/device (23). See FIGS. 13C, E. The use of alternating positive and negative pressure air pulses allows a full push-and-pull cycle, rather than the push-and-relax characteristic of other driver sources. Furthermore, the pump interface (15) between the pneumatic pump (12) and cartridge (24) is quite simple. A flexible tube (25) carries the pressure wave, diverting it around any internal obstacles, and delivers it to an outlet (26) configured for interface with a compressible grommet (27). Rigid chimney (14) molded into the polycarbonate plate (9) mates with this opening and transfers the pulse through a narrowed baffle (28) and into beveled underside (29), which in turn mates in conforming fashion with cartridge diaphragm (11) upon supply of a negative pressure/vacuum pulse from pump (12). See FIGS. 4,11.

With reference to FIGS. 4, 5, 8, and 11, rectified flow requires diaphragm pump zone to be communicatively flanked by a plurality of cooperating check valves, here two. One embodiment incorporates what is referred to as a "bridge" valves. Similar in concept to the common reed valve, a bridge valve functions by seating a flat, flexible bridge beam (13) across a port (31) and valve seat (30) in a rigid or substantially rigid substrate. When a pressure differential pulls the fluid through port (31), then flexible membrane (11) flexes away and allows fluid to pass around it. When the direction of the pressure differential reverses, the membrane gets pulled flat against the rigid valve seat and seals the port

(31) against backwash. In one embodiment, the flexible bridge beam (13) is formed from the same laminate layer (8a) that creates the channel ceiling and diaphragm (11). The valve seats (30) are preferably molded into the polycarbonate plate (9) and have slightly raised annular bosses relative to membrane (11) that facilitate sealing when in closed position. The bridge valve has a simple construction that does not require small floating parts or separate small pieces, which leads to easier manufacture and greater reliability. The bridge valve is more manufacturable even than its cousin, the reed valve. The "bridge" is constrained on both sides—on both "shores" if you will—whereas the reed would be attached on one side and free on the other (like a diving board or flap), open to being bent or folded over during assembly (and thus subject to fatigue/weakening). The bridge valve has another advantage over the reed valve in that it can be biased open, neutral, or closed. This is controlled by the relative placement of the flexible membrane and the rigid valve seat. If the flat, relaxed bridge is exactly flush against the seat, the bias is neutral; if the relaxed bridge is separated from the seat, the bias is open; if the valve seat protrudes so that the relaxed bridge is stretched and pressed against it, the bias is closed. The common reed valve cannot be biased closed.]

One distinct feature of the cartridge over the CFCD cartridge is the utilization of microfluidic technology to introduce fluidic circulation in order to accelerate hybridization and decrease the hybridization time. The microfluidic component consists of a plastic plate and a multi-layer laminate sandwich, which form functional microfluidic components such as a micropump, two check valves, and a hybridization channel. The laminate consists of multiple layers of silicone adhesive, Teflon, and a PET (polyethylene terephthalate) layer. The PET layer embodies two thin membranes in a bridge configuration that function as check valves and a diaphragm which is part of a pneumatically driven pump. A serpentine channel (275 um deep and 1 mm wide) within the laminate assembly forms the hybridization chamber above the working electrode array. The pneumatic pump is connected to a pneumatic source from the instrument. The pneumatic pump provides unidirectional pumping of the analyte through the serpentine channel past all the electrodes during the hybridization. Previous studies have shown that flow circulation in the hybridization channel brought a large number of target molecules per time unit to pass by individual electrodes and allowed continuously replenishing the area around the electrode that has been depleted of complementary targets. Moreover, since hybridization is a rate limiting process that relies on diffusion of target molecules across the diffusion boundary layer to their binding sites, the rapid fluid movements can enhance the transport of target within the diffusion boundary layer by reducing the thickness of the diffusion boundary layer. As a result, the hybridization kinetics is greatly improved and hybridization time is reduced from 2 hr to 30 min."

In operation, and with particular reference to FIGS. 2,3, 4 and 11, fluid is introduced to the cartridge (24) by way of a filling reservoir (16) molded into the polycarbonate plate (9). The underside of the outlet from this reservoir provides the valve seat (30) that together with bridge beam (13) forms the first bridge valve. Fluid flows out of the reservoir (16), across this valve and into a diaphragm chamber (22). From the diaphragm chamber (22) fluid is diverted back up through the polycarbonate plate (9) and across an overpass (34) so it can return to the second bridge valve, exiting through a second valve seat (30) and traversing a second bridge beam (13) to enter the primary channel (10). Fluid flows through this channel (10) over the electrodes (4) until it is released back into the filling/sample reservoir/chamber (16) where it is naturally stripped of bubbles before it begins another circuit. A jumper laminate (35) seals the oval recess (36) in plate (9) associated with overpass (34) and second valve seat (30) and is planar and proximate to the ends of two substantially parallel ports (72), which act to re-direct fluid from one plane to another in cartridge (24) and facilitate rectified valve-actuated flow by taking advantage of gravity. Jumper laminate (35) conforms substantially to the dimension of the oval overpass recess (36) and is affixed by a jumper laminate pressure sensitive adhesive layer (33) of conforming dimension. See FIGS. 2,3. Any dimension other than oval can be used, e.g., square, rectangular, circular. A separate molded polypropylene cap (38) with a living hinge (39) provides a seal for the filling reservoir. A rigid cover (40), also made from molded polycarbonate, fits over the top of the polycarbonate plate (9). It incorporates detents (41) to hold the PCB alignment features against their mating partners within the module (42) (discussed below) and to provide tactile and/or audible feedback. Cover (40) also includes a handle (43) for easy manipulation in and out of module (42), keying features to ensure appropriate orientation before clamping the cartridge into the instrument, and clearance hole/recess (45) for receipt of chimney (14) and for easy viewing of the filling/sample reservoir (16). A large, flat area (47) on the cover's surface interfaces with the module clamping mechanism discussed below, and internal ribs (underside of cover; not shown) transfer the pressure evenly across the polycarbonate plate (9). Space spanned by these ribs affords adaptability for future inclusion of one or more additional functionalities. Cover (40) is made of polycarbonate (injection-molded) and has a recess (49) to accommodate the fill reservoir/chamber (16) of plate (9). The combined plate/assembly is attached to cover (40) by way of two bosses (67) on plate that have reciprocal engagement recesses in the underside of cover. See FIGS. 1A,B and 2. Each of laminate assembly (2), plate (9) and individual laminate layers (8) and adhesive layers (7) also have an EEPROM recess/void (70) for allowing access to the EEPROM (6).

The laminate assembly (2) and rigid plate (9) are both preferably made of polyethyleneterepthalate (PET) and etched polytetrafluoroethylene (PTFE), and one or more of the individual laminate layers and PCB board are held together by pressure sensitive adhesive (PSA) membranous layers, preferably silicone-based. Other laminates that can be used include but are not limited to, e.g., polycarbonate, polyethylene, ultra high molecular weight polyethylene (UHMW PE) and polypropylene. Criteria for an acceptable laminate include one or more of flexibility (tensile modulus), conformability (form by cold flow), pliability, ability to cut/machine or ablate (laser), ability to slice/make thin (form into a film), durability, heat stability, and chemical inertness relative to the fluidic components and assay chemistry therein. In addition, in place of one or more laminates, silicone layers can be used that have resilience/pliability and compressibility to facilitate sealing. The materials used for construction are readily available commercially: Adhesive layers of thicknesses 0.001-0.003" from silicone pressure sensitive adhesives, for example, Tran-Sil NT1001 pressure sensitive adhesive of thickness 0.002" (Dielectric Polymers INC, Holyoke Mass.). Flexible materials such as skived Teflon® (PTFE) film of thickness 0.002-0.010" come from Fralock, Valencia Calif., and polycarbonate, polypropylene, and PET films 0.0005"-0.005" thick come from Now Plastics, INC, East Longmeadow Mass. Pump specs: Micro Diaphragm, KNF Neuberger GmbH (Freiburg, DE), PU1947-NMP09-1.07, 6 Volts. These and other parts and materials are generic and commercially available or known in the art, or else readily produced and assembled by the person of ordinary skill in the art with the guidance of the present disclosure.

The dimensions of the flow channel are significant in that the linear speed of the fluid over the electrodes is dependent on the channel cross section. Additionally, the channel height and width must be great enough to allow any bubbles to freely flow through the channel and eventually be trapped/cleared in the reservoir. Therefore, it is important to design a channel that is small enough to provide sufficient linear velocity but not too restrictive with respect to bubble movement. Another consideration is that the lower channel dimensions will utilize less analyte solution, often a desired characteristic. Channel widths of 0.030-0.060" and heights of 0.006"-0.0014" were tested as compatible ranges, with the preferred dimensions being a width of 0.040" and height of 0.010".

The overall channel dimensions directly impact the minimum amount of fluid required to flow without lapses in analyte fluid (large bubbles/gaps) in the system. However, amounts in excess of the channel volume can be cycled through the reservoir. The preferred system as described above allows for analyte volumes of about 1100-200 uL, preferably about 130 uL or less. This range can be tuned easily by increasing or decreasing the channel height via the thickness of laminate assembly and contributing layers.

The dimensional aspects require exacting manufacturing methods such as the use of laser cutting machinery instead of die cutting, as die cutting cannot form the thin channels (width of 0.030-0.040") preferred. However, die-cutting could be used for laminates with features at the upper ends of the suggested ranges, e.g., 0.060".

Material compatibility was thoroughly tested for Tran-Sil adhesives, with PET and PTFE Teflon® membrane components. The preferred laminate assembly consists of 0.003" Transil® adhesive applied to the one side of 0.006" Teflon® (the side to be adhered to the PCB), another Tran-Sil® layer of 0.002" thickness between the other side of the Teflon® the 0.001" PET middle laminate containing the bridge valves. The final adhesive layer of 0.002" Transil® is applied to the PET laminate and eventually bonds the polycarbonate cover to the laminate and PCB.

Example 2

Cartridge Module Design & Manufacture

Figure 7:
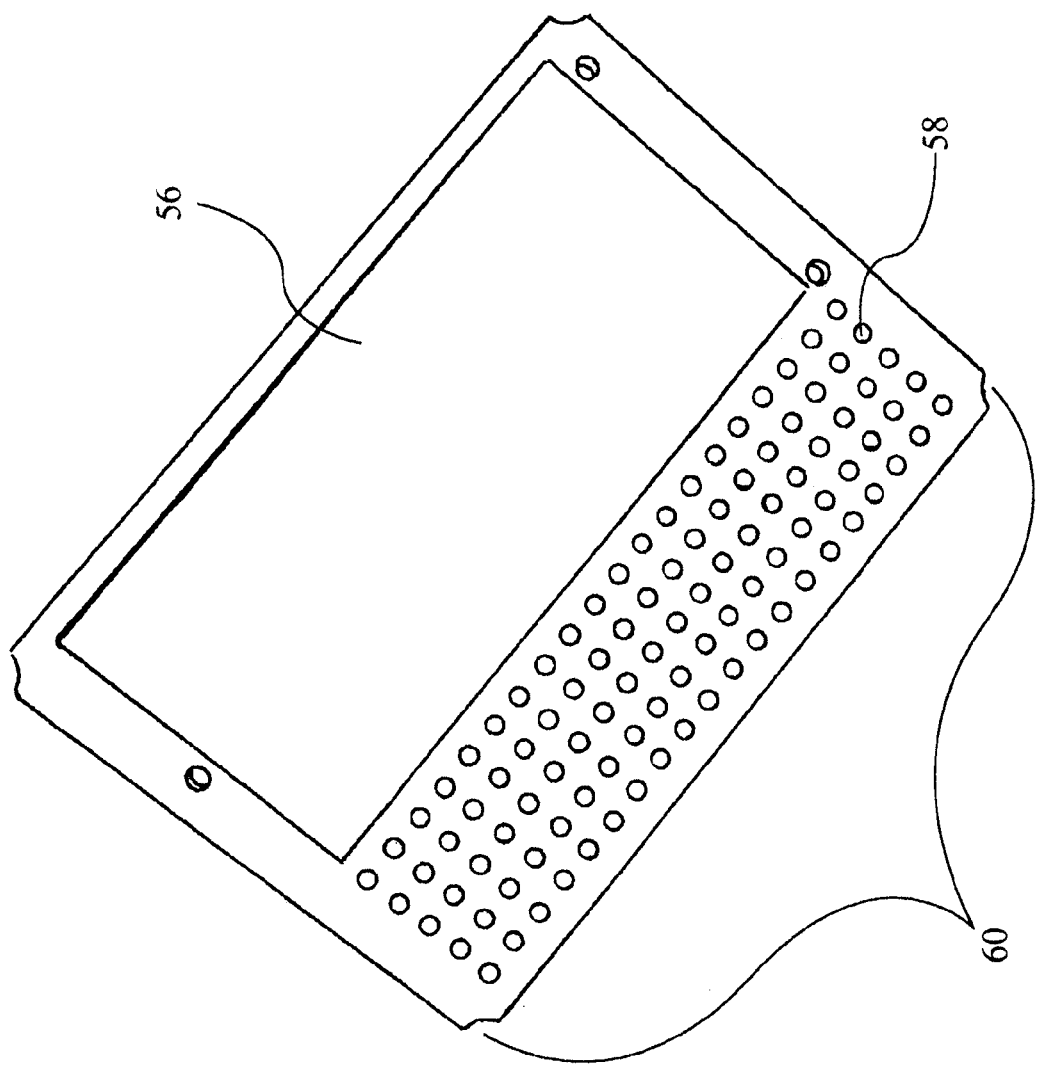
FIG. 7 shows the underside view of FIG. 6, including connector pads and rectangular area showing the thermal interface location for receipt of a temperature-controlled metal plate thereover. There are also alignment features (cutouts or "cookie bites") shown to facilitate proper connection to the connector. The connector pads are clamped into a detection device preferably using a zero-insertion force (ZIF) mechanism. In another embodiment, the connector pads may be concentrated in mass on a side facing ("edge" connectors).
Figure 8:
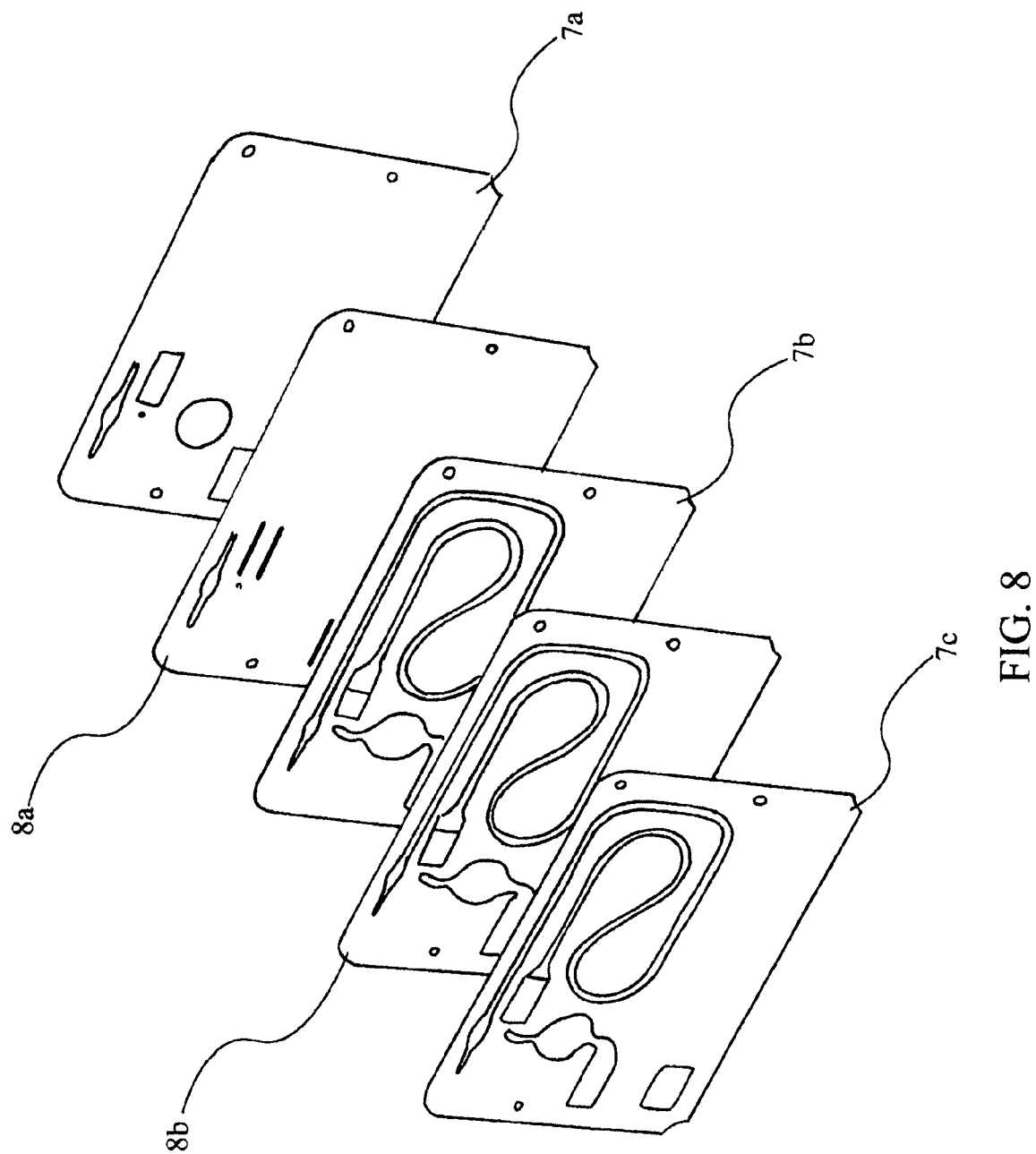
FIG. 8 shows individual modular laminate components of the laminate assembly, each having features cooperative with and complementary to each other when in operative use. The top piece is an adhesive layer with voids for functional overlay over the middle laminate which contains bridge valve slits and orifices that cooperate with those on the lower laminate/adhesive to form functional diaphragm, valves and channels. The lower piece is a laminate covered on both sides with an adhesive layer, the bottom of which mates with the PCB board.
Figure 9:
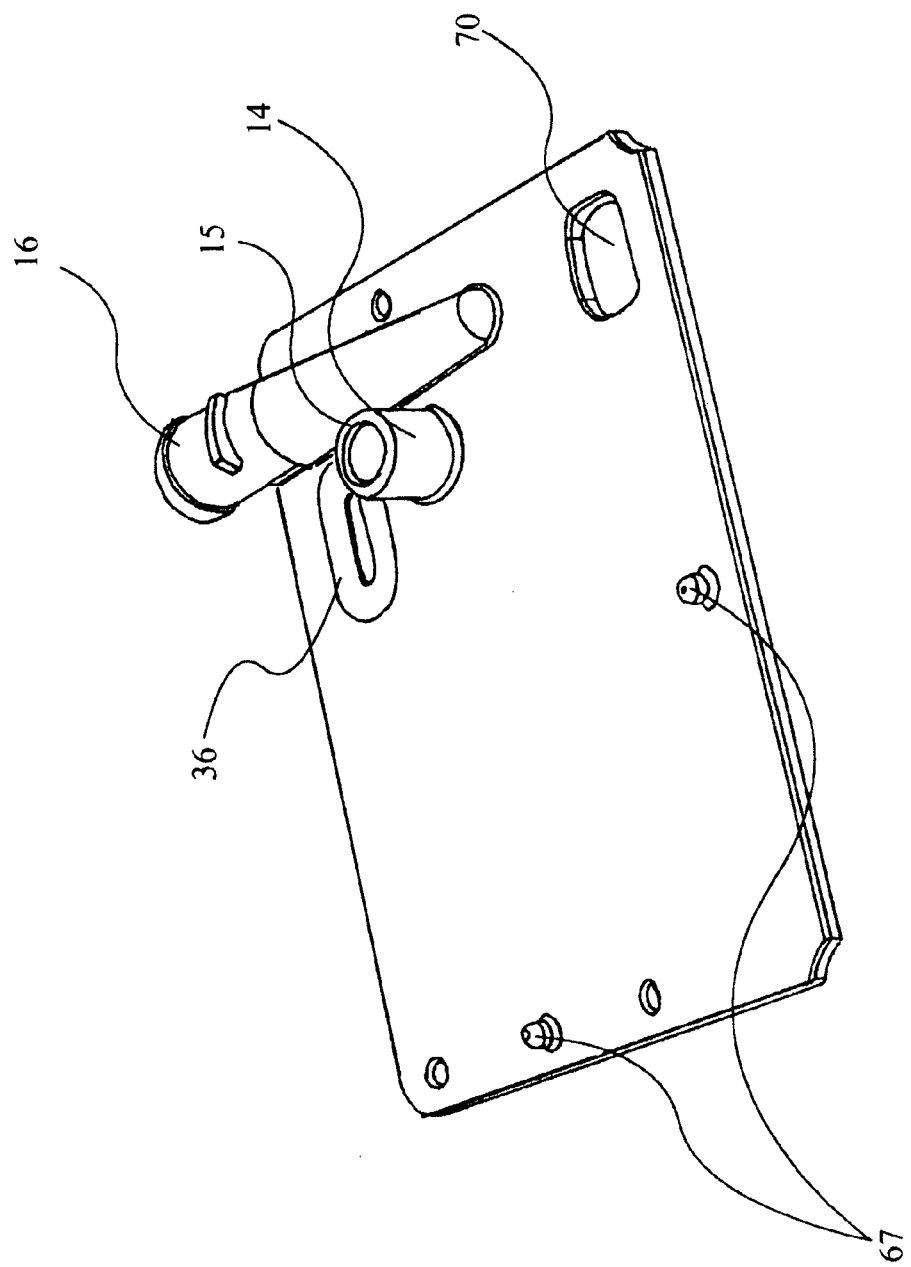
FIG. 9 is a top perspective view of the plate, which houses the sample fill reservoir, pump interface, void for receipt of an EEPROM and oval recess over which is sealed a jumper laminate. Also shown are raised bosses that facilitate engagement of plate to cover.

With reference to FIGS. 13A-E, the interface between detection device (23) and cartridge (24) is mediated by a cartridge module (42), which consists of a base (50) and top (51), both of which are made of molded polyetherimide plastic (glass-filled Ultem®, General Electric), and both of which contain aligned embedded metal screw castings (52) for fastening to each other. Module top (51) contains a connector lever (53) and engagement plate (54) for slideably engaging and disengaging cartridge firmly against base (50) and buckle beam assembly (73) electrical connection points therein. Top (51) also contains a conduit (55) for mating with the cartridge chimney (14) and feeding and withdrawing air to and from said cartridge. Base (50) has a heater area (56) for receiving and mating with a gold/nickel plated copper thermal plate (57) and buckle beam assembly (73) that consists of an array of gold/nickel plated beryllium copper pins parallel and proximate to said heater area (56) for electrically engaging contact pads (58) beneath PCB (1) (see FIG. 7), and two spring-loaded stainless steel metal detent locating pins (59) and radii (60) to aid final functional positioning of cartridge upon initial positioning into module (42). Thermal plate (57) overlays heater area (56) and presses against the flat underside of the PCB (1) directly beneath cartridge fluid channel (10) to act as a modulable heat source for reactions taking place therein.

The electrical interface between device and cartridge relies on reciprocally cooperating features possessed by both. See FIGS. 7, 13A-D. In the PCB (1), traces (not shown) are routed from the electrodes (2-5) through vias (not shown) to the underside of the PCB (1), where the two-dimensional array of gold contact pads (58) are exposed to said buckle beam assembly (73), individual pads mating with individual pins thereon. Module (42) is a clamping zero-insertion-force (ZIF) connector wherein the cartridge is slotted in loose and then firmly engaged within module (42) upon positionment against detent pins (59) and radii (60) and clamping with slideable lever (53) that forces engagement plate (54) down against top of cartridge (24), thereby securing bottom of cartridge (24), including pads (58), firmly against buckle beam assembly (73). Clamping motion also forcibly mates compressible outlet (63) of pneumatic conduit (55) with cartridge chimney (14). Alignment features (64) cut into the PCB ensure that the array of pads (58) on underside of the PCB (1) and the array of pins from buckle beam assembly (73) line up.

Buckle beam contacts can be substituted by pogo pins, anisotropic electrically conductive tapes, films, elastomers, and or other connectors known in the art. Elastomeric parts for pneumatic interface, including compressible outlet, are made of molded polyurethane, but silicone and like compositions are also considered to be an adequate alternative.

Example 3

Detection Device

Figure 14:
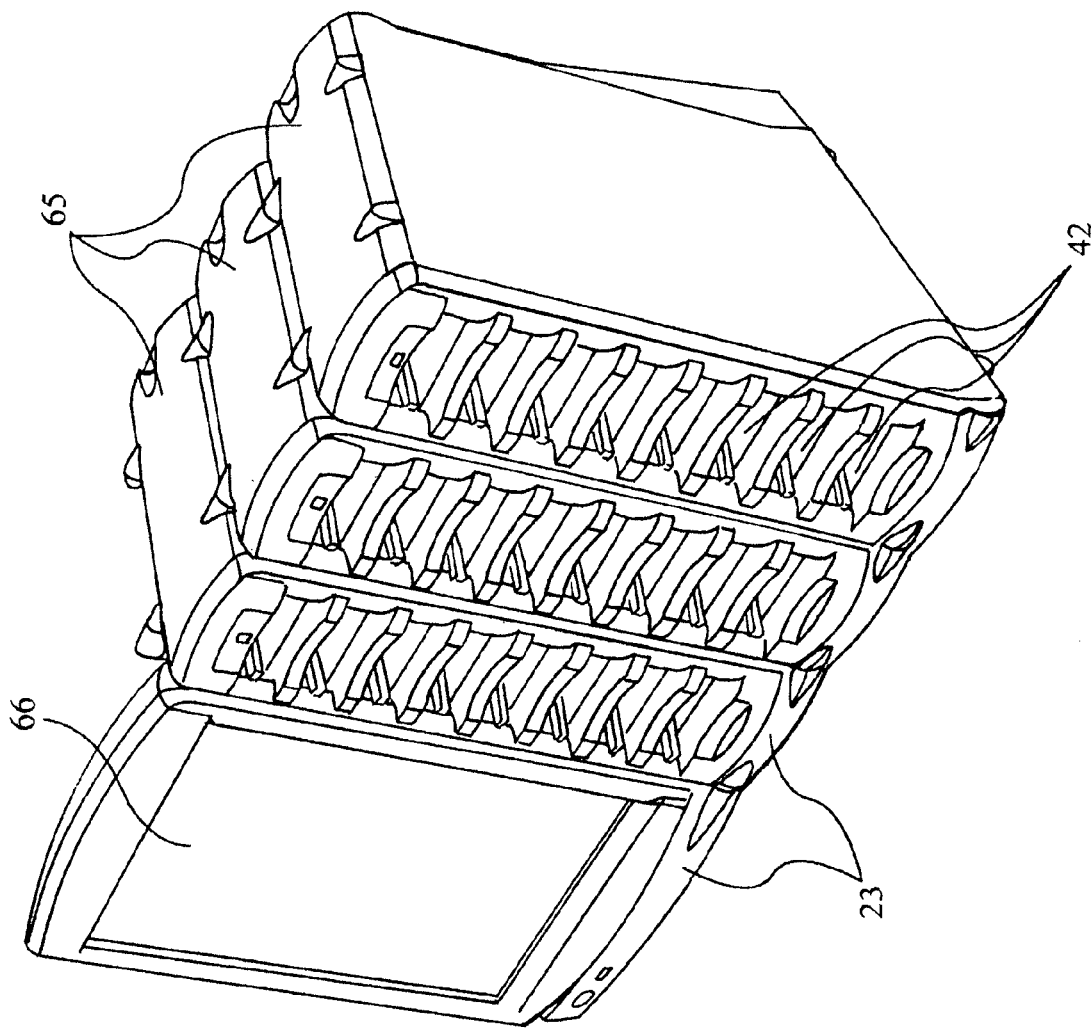
FIG. 14 shows an embodiment of a detection device for housing multiple cartridges according to the invention.

In typical use, and with reference to FIG. 14, the cartridge and cartridge module are coupled to a detection device (23) and/or computer, which parts may be combined into one, as is known and readily implementable in the art. FIG. 14 shows an embodiment of a detection device (23) for housing multiple cartridges (24). This embodiment contains three vertical towers (65) each possessing eight cartridges (24), each of which fits into its own module (42). To the left is a computer screen (66) for programming detection parameters and evaluating results. In this particular embodiment the screen is a touch-pad screen from which a user may conveniently select from various programming options merely by touching the screen. The fill reservoir/chambers (16) of the cartridges (24) face out at an approximate 15° angle relative to horizontal to take advantage of gravity and 3-dimensional space to economize/optimize onlooker or technician view and facilitate loading/clamping of cartridges into cartridge modules. For maximum utility, the detection device is programmed to perform either a random-access or batch mode operation, which allows for one or more different tests to be run simultaneously.

The preceding is useful for any detection device. Specifics of electrochemical detection and other detection methods are as described previously and in the above-cited documents.

All articles and documents referenced herein, as well as all the citations cited therein, are incorporated by reference for an understanding of the invention and are indicative of what the person of ordinary skill requires to know to make the invention operable using no more than routine experimentation, as well as appreciate the advantages of the invention.

One skilled in the art will readily appreciate that the present invention is well adapted to carry out the objects and obtain the ends and advantages mentioned, as well as those inherent therein. The methods and compositions described illustrate preferred embodiments, are exemplary, and are not intended as limitations on the scope of the invention. Certain modifications and other uses will be apparent to those skilled in the art, and are encompassed within the spirit of the invention as defined by the scope of the claims.

The terms and expressions which have been employed are used as terms of description and not of limitation, and there is no intention in the use of such terms and expressions of excluding any equivalents of the features shown and described, or portions thereof. It is recognized that various modifications are possible within the scope of the invention claimed. Thus, it should be understood that although the present invention has been specifically disclosed by preferred embodiments, optional features, modifications and variations of the concepts herein disclosed may be resorted to by those skilled in the art, and that such modifications and variations are considered to be within the scope of this invention as defined by the description and the appended claims.

In addition, where features or aspects of the invention are described in terms of ranges or Markush groups or other grouping of alternatives, e.g., genuses, those skilled in the art will recognize that the invention is also thereby described in terms of any individual measurement, member or subgroup of members of the range, Markush group or subgenus, and exclusions of individual members as appropriate, e.g., by proviso.

What is claimed:

1. A fluidics device comprising:
a flow channel for transporting a fluid sample;
an inlet port for receiving said fluid sample, said inlet port in fluid communication with a first bridge valve;
a diaphragm configured and adapted to interface with a pump, said diaphragm being coupled to said first bridge valve;
a second bridge valve in fluid communication with said flow channel, said second valve being coupled to said diaphragm,
wherein said diaphragm and said bridge valves are integral to a common membranous layer in a multilayer assembly, and
wherein each of said first bridge valve and said second bridge valves comprises a displaceable region between substantially parallel slits in the membranous layer, wherein the displaceable region allows said fluid sample to flow under or over said displaceable region according to a direction of displacement thereof.

2. The fluidics device of claim 1, further comprising a working electrode located in said flow channel.

3. The fluidics device of claim 2, further comprising an auxiliary electrode.

4. The fluidics device of claim 1, further comprising a connector configured and adapted to interface with a detection device.

5. The fluidics device of claim 1, further comprising an Electrically Erasable-Programmable Read-Only Memory (EEPROM).

6. The fluidics device of claim 1, further comprising a binding partner or a ligand immobilized in said flow channel.

7. The fluidics device of claim 6, wherein said binding partner or ligand is immobilized using a self-assembling monolayer that is affixed to an electrode surface.

8. The fluidics device of claim 6, wherein said binding partner or ligand is selected from the group consisting of a polynucleotide, a protein, a peptide, an antibody, and a combination thereof.

9. The fluidics device of claim 1, further comprising an array of electrodes, each bound to a binding partner or a ligand.

10. The fluidics device of claim 9, wherein said electrode array comprises a plurality of different binding partners and/or ligands immobilized thereon.

11. The fluidics device of claim 9, wherein said electrode array is located in a serpentine channel.

12. The fluidics device of claim 1, wherein said flow channel comprises a cross-sectional dimension comprising a greater width than height.

13. The fluidics device of claim 1, having a sample capacity ranging from about 50 μL to about 200 μL.

14. The fluidics device of claim 9, having a single cartridge capacity of no more than about 200 μL, wherein said array is contained in a flow channel having a length ranging from about 100 mm to about 200 mm and a cross-sectional dimension ranging from about 0.75 mm to about 2.0 mm in width and about 0.125 mm to about 0.40 mm in height.

15. A diagnostic kit comprising the fluidics device of claim 1.

16. A method of determining analyte binding, comprising:
providing the fluidics device according to claim 9;
adding to said device the fluid sample, wherein the fluid sample is suspected of containing an analyte specific for said binding partner or ligand;
circulating and recirculating said fluid sample across said electrode array; and
detecting binding of said analyte to said binding partner or ligand.

17. The method of claim 16, wherein said circulating and recirculating is performed at a rate ranging from about 10 μL/sec to about 40 μL/sec.

* * * * *